US012605318B2

(12) United States Patent
Clarke et al.

(10) Patent No.: US 12,605,318 B2
(45) Date of Patent: Apr. 21, 2026

(54) SYNERGISTIC PRESERVATIVE/PERSONAL CARE COMPOSITION CONTAINING AN ALKYLENE GLYCOL ESTER

(71) Applicant: Arch UK Biocides Ltd, Blackley (GB)

(72) Inventors: James Clarke, Blackley (GB); Louise Reay, Blackley (GB); Samantha Jane Thomas, Blackley (GB); Philip Lewis Roebuck, Blackley (GB); Jake Campbell, Blackley (GB); Neil Scott Shaw, Blackley (GB)

(73) Assignee: Arch UK Biocides Ltd, Blackley (GB)

( * ) Notice: Subject to any disclaimer, the term of this patent is extended or adjusted under 35 U.S.C. 154(b) by 692 days.

(21) Appl. No.: 17/920,493

(22) PCT Filed: Apr. 22, 2021

(86) PCT No.: PCT/EP2021/060549

§ 371 (c)(1),
(2) Date: Oct. 21, 2022

(87) PCT Pub. No.: WO2021/214234

PCT Pub. Date: Oct. 28, 2021

(65) Prior Publication Data

US 2023/0141915 A1 May 11, 2023

(30) Foreign Application Priority Data

Apr. 23, 2020 (EP) .................................... 20171210

(51) Int. Cl.

| | |
|---|---|
| ***A61K 8/34*** | (2006.01) |
| ***A61K 8/36*** | (2006.01) |
| ***A61K 8/365*** | (2006.01) |
| ***A61K 8/368*** | (2006.01) |
| ***A61K 8/37*** | (2006.01) |
| ***A61K 8/41*** | (2006.01) |
| ***A61K 8/49*** | (2006.01) |
| ***A61Q 19/00*** | (2006.01) |

(52) U.S. Cl.

CPC ................ *A61K 8/375* (2013.01); *A61K 8/34* (2013.01); *A61K 8/36* (2013.01); *A61K 8/365* (2013.01); *A61K 8/368* (2013.01); *A61K 8/41* (2013.01); *A61K 8/416* (2013.01); *A61K 8/49* (2013.01); *A61K 8/498* (2013.01); *A61Q 19/00* (2013.01); *A61K 2800/10* (2013.01); *A61K 2800/524* (2013.01)

(58) Field of Classification Search

CPC . A61K 8/375; A61K 8/34; A61K 8/36; A61K 8/365; A61K 8/368; A61K 8/41; A61K 8/416; A61K 8/49; A61K 8/498; A61K 8/19; A61K 8/23; A61K 8/27; A61K 8/345; A61K 8/361; A61K 8/362; A61K 8/42; A61K 8/44; A61K 8/4906; A61K 8/347; A61K 2800/10; A61K 2800/524; A61Q 19/00; Y02A 40/90

See application file for complete search history.

(56) References Cited

U.S. PATENT DOCUMENTS

| | | | |
|---|---|---|---|
| 4,816,256 A | 3/1989 | Randen | |
| 5,460,833 A | 10/1995 | Andrews et al. | |
| 5,569,461 A * | 10/1996 | Andrews | A61K 9/0041 424/405 |
| 6,033,705 A | 3/2000 | Isaacs | |
| 2003/0017176 A1 | 1/2003 | Bleckmann et al. | |
| 2009/0163445 A1 | 6/2009 | Diehl et al. | |
| 2016/0058775 A1 | 3/2016 | Prasad et al. | |
| 2016/0194819 A1 | 7/2016 | Zhang et al. | |
| 2016/0331848 A1 | 11/2016 | Moro et al. | |
| 2017/0354116 A1* | 12/2017 | Gradle | A01N 37/16 |
| 2018/0207122 A1 | 7/2018 | Scholz et al. | |
| 2019/0142800 A1 | 5/2019 | Ghosh et al. | |
| 2020/0030276 A1 | 1/2020 | Scholz et al. | |

FOREIGN PATENT DOCUMENTS

| | | |
|---|---|---|
| CN | 101151016 | 3/2008 |
| CN | 108125797 | 6/2018 |
| JP | 2001261914 A * | 9/2001 |
| WO | WO2014144891 | 9/2014 |

OTHER PUBLICATIONS

Asai, N. JP 2001-261914 A human-assisted machine translation, Translations Branch, STIC, USPTO (Jun. 2, 2025) (Year: 2025).*
Lincoln MFG-USA, Lincoserve PE610 Datasheet (Apr. 10, 2020) (Year: 2020).*
ChemLin (2018). "PEG-7 Glyceryl Cocoate." Internet Chemistry. Retrieved on Jun. 2, 2025 from https://www.internetchemie.info/chemie-lexikon/stoffe/p/peg-7 glyceryl cocoate.php. (Year: 2018).*
GEA North America "Effinity Non-Iodine Post Milking Teat Dip." GEA, Feb. 5, 2020, Retrieved on Jun. 4, 2025 from https://cdn.gea.com/-/media/migratedfromtridion/static-downloads/country/us/campaign/effinity-teat-dip-brochure-65727.pdf?rev=9428fd79d6ca4af68fcfc2061f44ac94. (Year: 2020).*
European Search Report for 20171210.6 dated Oct. 2, 2020, 14 pages.
"Innovation Zone—Discover the latest ingredients, formulations and the most innovative beauty products", asia.in-cosmetics.com, Nov. 1, 2012 pp. 1-44,https://asia.in-cosmetics.com/rxuk/rxu k_in-cosmeticsasia/files/final_6311_incos_asia_innovation_guide_a4_2012_vI0_lo.pdf?v=634904876498724542.
International Preliminary Report on Patentability for PCT/EP2021/060549 dated Jul. 12, 2022, 27 pages.

(Continued)

*Primary Examiner* — Amanda L. Aguirre

(74) *Attorney, Agent, or Firm* — Dority & Manning, PA

(57) ABSTRACT

Provided herein are preservative compositions containing a preservative agent with an alkylene glycol ester. Also provided are method for increasing the efficacy of preservative agents and methods for reducing the minimum amount of preservative agent needed for effective preservation activity in end-use formulations.

32 Claims, No Drawings

(56) References Cited

OTHER PUBLICATIONS

International Search Report and Written Opinion for PCT/EP2021/060549 dated Jul. 2, 2021, 23 pages.

* cited by examiner

SYNERGISTIC PRESERVATIVE/PERSONAL CARE COMPOSITION CONTAINING AN ALKYLENE GLYCOL ESTER

RELATED APPLICATIONS

The present application is the National Stage entry of International Patent Application No. PCT/EP2021/060549, filed on Apr. 22, 2021, which is based on and claims priority to European Patent application Serial No. 20 171 210.6, filed on Apr. 23, 2020.

FIELD OF INVENTION

The present invention relates to a preservative composition containing a preservative agent and a potentiator ingredient with enhance preservative properties as compared with a preservative composition with a preservative agent itself.

BACKGROUND OF THE INVENTION

Microbial contamination of personal care products, cosmetics, home care products and other similar products is a matter of great importance to the personal care industry. Microbial contamination can become a major cause of product losses of end-use formulations and can cause significant economic loss. Further, contamination of cosmetics and home care products can result in their being converted into products that are hazardous for consumers. Certain, preservative agents and preservative compositions for protecting against microbial attack either from bacterial or fungal sources are known in the art. These preservative agents have a wide variety of applications in fields such as personal care products, cosmetics, home care products, and health and hygiene products.

There are continued regulatory pressures to reduce the amount of the preservative agent(s) in end-use formulations. Similarly, in the field of personal care formulations there are ongoing regulatory pressures to reduce the amount of the active ingredient in personal care formulations. Additionally, there are continued regulatory pressures to stop using certain conventional preservatives or to reduce the amount of certain conventional preservatives in end-use formulations.

Accordingly, a need exists for preservative compositions that contain less active ingredient or preservative while maintaining acceptable levels of overall antimicrobial efficacy.

SUMMARY OF THE INVENTION

Provided herein is a synergistic mixture of a preservative agent with an alkylene glycol ester compound which can be used in various compositions, including personal care formulations.

In one aspect, provided is a preservative composition containing a (i) preservative agent; and (ii) an alkylene glycol ester, wherein the alkylene glycol ester is present in an amount to sufficiently increase the efficacy of the preservative agent as compared to the preservative agent alone, and the increase is greater than the additive effect of the biocidal activity of the preservative agent and alkylene glycol ester taken alone.

In another aspect, provided is a preservative composition according wherein the weight ratio of the alkylene glycol ester to the preservative agent, for instance, can be in the range of about 1:50,000 to about 500:1, such as from about 1:10,000 to about 300:1, such as from about 1:5,000 to about 10:1, such as from about 1:2,500 to about 8:1, such as from about 1:1,500 to about 2:1. In many applications, only a small amount of alkylene glycol ester is needed in order to enhance the efficacy of the preservative agent. For example, in one aspect, the preservative agent is present in greater amounts than the alkylene glycol ester. In certain embodiments, the weight ratio of the alkylene glycol ester to the preservative agent can be from about 1:5,000 to about 4:1, such as from about 1:1,500 to about 4:1, such as from about 1:300 to about 4:1, such as from about 1:20 to about 4:1, such as from about 1:15 to about 4:1, such as from about 1:10 to about 4:1.

In another aspect, the preservative composition has a preservative agent which is an acid compound, an aldehyde, a phenolic compound, a sulfite, an iron chelator, an aromatic alcohol, a quaternary ammonium compound, a pyrone compound, a urea compound, an imidazole compound, an isothiazolinone compound, an amine such as a triamine or a combination of two or more preservative agents.

In a particular aspect, the preservative composition has a preservative agent containing an iron chelator, said iron chelator comprises a pyrithione compound, piroctone olamine, 2-pyridinol-1-oxide, N-hydroxy-6-octyloxypyridine 2(1H)-one, -hydroxy-6-octyloxypyridine 2(1H)-one ethanolamine salt or a mixture thereof. Particular pyrithione compounds include zinc pyrithione, sodium pyrithione or mixtures thereof.

In an embodiment of the present invention, the preservative agent is an acid compound. The acid compound may be an acid, an ester of an acid or a salt of an acid. In a particular embodiment, the acid compound comprises benzoic acid, propionic acid, salicylic acid, sorbic acid, formic acid, undec-10-enoic acid, lactic acid, glycolic acid, and citric acid, or a salt thereof.

In another embodiment, the preservative agent is a quaternary ammonium compound. Particular quaternary ammonium compounds include an alkyl (C12-22) trimethyl ammonium compound, a benzethonium compound, or a mixture thereof.

In a further embodiment, the preservative agent comprises an alcohol. Alcohols may include lower alkyl alcohols or aromatic alcohols. A particular aromatic alcohol is phenoxy ethanol and a particular lower alcohol is isopropanol.

In another aspect, the alkylene glycol ester can be a monoalkylene glycol ester, a dialkylene glycol ester, a trialkylene glycol ester or mixtures thereof. The alkylene glycol ester can be formed from a C1 to C6 alkylene, such as ethylene, propylene, or butylene. The alkylene glycol ester can be a monoester, a diester, or mixtures thereof and can be derived from (a) an alkylene glycol, and (b) a fatty acid comprising, for example, a caproic acid, caprylic acid, capric acid, lauric acid, myristic acid, or palmitic acid. Particular examples of such alkylene glycol esters include one or more of an alkylene glycol isostearate, an alkylene glycol laurate, an alkylene glycol myristate, an alkylene glycol oleate, an alkylene glycol monolaurate, an alkylene glycol monocaprate, an alkylene glycol monocaprylate, an alkylene glycol caproate, an alkylene glycol diperlargonate, an alkylene glycol diisostearate, an alkylene glycol dilaurate, an alkylene glycol monopalmitate, an alkylene glycol monostearate, an alkylene glycol decanoate, or mixtures thereof, other complexes or derivatives thereof, and the like. The alkylene group in the above examples can be one or more propylene groups, ethylene groups or butylene groups. In one embodiment, at least one alkylene glycol monoester is incorporated into the composition.

In another aspect of the present invention, provided is method for increasing the efficacy of a preservative agent in an end-use formulation. The method contains the steps of providing a preservative agent and an effective amount of an alkylene glycol ester. The preservative agent and alkylene glycol ester can be added to an end-use formulation to increase the efficacy of the preservative agent as compared to an equal amount of preservative agent without the alkylene glycol ester. The alkylene glycol ester may be added to the preservative agent prior to the addition of the preservative agent to the end-use formulation, after the preservative agent is added to the end-use formulation, prior to the addition of the preservative agent to the end-use formulation, or concurrently with the preservative agent to the end-use formulation.

In a further aspect of the present invention, provided is a method of increasing the resistance of an end-use formulation to biological attack. The method includes providing a cosmetic formulation and adding a preservative composition in any one of the previous aspects or embodiments to the cosmetic formulation. By adding the preservative composition, the end use composition has an increased resistance to biological attack as compared to an end-use formulation without the alkylene glycol ester present in the preservative composition.

In a further aspect of the present invention, provided is a method of reducing the minimum amount of preservative agent needed for effective preservation activity in an end-use formulation. The method includes providing a preservative agent and adding an amount of an alkylene glycol ester to the preservative agent to form a preservative composition. The preservative composition can then be added to an end-use formulation, wherein the minimum amount of the preservative agent needed for effective preservation activity in the end-use formulation is less than if the preservative agent was used alone.

In a further embodiment, provided is an end-use formulation containing a preservative composition of any of the prior embodiments. The end-use formulation may be a personal care formulation or a home care formulation.

In a further aspect, the present invention provides a preservative composition comprising (i) a preservative agent selected from the group consisting of phenoxyethanol, bis (3-aminopropyl) dodecylamine, didecyl dimethyl ammonium chloride, sodium benzoate, lactic acid, benzyl alcohol, benzisothiazolinone, sorbic acid, and dehydroacetic acid, or a salt thereof; and (ii) at least one alkylene glycol ester derived from (a) an alkylene glycol, and (b) a fatty acid having from about 6 to 14 carbon atoms, wherein the at least one alkylene glycol ester is present in an amount to sufficiently increase the efficacy of the preservative agent as compared to the preservative agent alone.

In one embodiment, the preservative agent is phenoxyethanol and preferably the phenoxyethanol and the at least one alkylene glycol ester are comprised in the preservative composition at a weight ratio of from 6:1 to 1:1, preferably of from 3:1 to 1:1, more preferably of from 2:1 to 1:1.

In one embodiment, the preservative agent is bis (3-aminopropyl) dodecylamine and preferably the bis (3-aminopropyl) dodecylamine and the at least one alkylene glycol ester are comprised in the preservative composition at a weight ratio of from 25:1 to 1:25, preferably of from 20:1 to 1:20, more preferably of from 15:1 to 1:15.

In one embodiment, the preservative agent is didecyl dimethyl ammonium chloride and preferably the didecyl dimethyl ammonium chloride and the at least one alkylene glycol ester are comprised in the preservative composition at a weight ratio of from 25:1 to 1:25, preferably of from 20:1 to 1:20, more preferably of from 15:1 to 1:15.

In one embodiment, the preservative agent is sodium benzoate and preferably the sodium benzoate and the at least one alkylene glycol ester are comprised in the preservative composition at a weight ratio of from 50,000:1 to 50:1, preferably of from 10,000:1 to 100:1, more preferably of from 5000:1 to 150:1.

In one embodiment, the preservative agent is lactic acid and preferably the lactic acid and the at least one alkylene glycol ester are comprised in the preservative composition at a weight ratio of from 250:1 to 1:1, preferably of from 220:1 to 1:1, more preferably of from 200:1 to 2:1.

In one embodiment, the preservative agent is benzyl alcohol and preferably the benzyl alcohol and the at least one alkylene glycol ester are comprised in the preservative composition at a weight ratio of from 800:1 to 1:1, preferably of from 600:1 to 2:1, more preferably of from 400:1 to 3:1.

In one embodiment, the preservative agent is benzisothiazolinone and preferably the benzisothiazolinone and the at least one alkylene glycol ester are comprised in the preservative composition at a weight ratio of from 40:1 to 1:4, preferably of from 60:1 to 1:3, more preferably of from 40:1 to 1:2.

In one embodiment, the preservative agent is sorbic acid and preferably the sorbic acid and the at least one alkylene glycol ester are comprised in the preservative composition at a weight ratio of from 100:1 to 1:4, preferably of from 80:1 to 1:3, more preferably of from 60:1 to 1:2.

In one embodiment, the preservative agent is dehydroacetic acid and preferably the dehydroacetic acid and the at least one alkylene glycol ester are comprised in the preservative composition at a weight ratio of from 1000:1 to 10:1, preferably of from 800:1 to 15:1, more preferably of from 600:1 to 20:1.

In one embodiment, the present invention provides a preservative composition comprising (i) a preservative agent, wherein the preservative agent comprises phenoxyethanol; and (ii) at least one alkylene glycol ester derived from (a) an alkylene glycol, and (b) a fatty acid having from about 6 to 14 carbon atoms, wherein the at least one preservative agent and the alkylene glycol ester are comprised in the preservative composition at a weight ratio of from 1:1 to 6:1.

In one embodiment, the preservative agent is phenoxyethanol.

In one embodiment, the at least one alkylene glycol ester is a propylene glycol ester or a mixture of propylene glycol esters derived from (a) propylene glycol, and (b) a fatty acid having from about 6 to 14 carbon atoms. In one embodiment, the fatty acid is selected from the group consisting of caproic acid, caprylic acid, capric acid, lauric acid, myristic acid, and combinations thereof. In one embodiment, the at least one alkylene glycol ester is a monoester, a diester, or a combination thereof. In one embodiment, the at least one alkylene glycol ester comprises propylene glycol monocaprylate, propylene glycol dicaprylate, or a combination thereof.

In one embodiment, the phenoxyethanol and the at least one alkylene glycol ester are comprised in the preservative composition at a weight ratio of from 1:1 to 2:1, preferably at a weight ratio of from 1.2:1 to 1.8:1, and more preferably at a weight ratio of from 1.4:1 to 1.6:1.

In one embodiment, the at least one alkylene glycol ester comprises propylene glycol caprylate.

In one embodiment, the at least one alkylene glycol ester comprises a mixture of at least one propylene glycol monocaprylate and propylene glycol dicaprylate. In one embodiment, the at least one alkylene glycol ester consists of a mixture of at least one propylene glycol monocaprylate and propylene glycol dicaprylate.

In one embodiment, the at least one propylene glycol monocaprylate and the propylene glycol dicaprylate are comprised in the mixture at a weight ratio of from 15:1 to 1:1, preferably at a weight ratio of from 10:1 to 1:1, more preferably at a weight ratio of from 5:1 to 2:1.

In one embodiment, the phenoxyethanol and the mixture of at least one propylene glycol monocaprylate and propylene glycol dicaprylate are comprised in the preservative composition at a weight ratio of from 1:1 to 2:1, preferably at a weight ratio of from 1.2:1 to 1.8:1, and more preferably at a weight ratio of from 1.4:1 to 1.6:1.

In one embodiment, the at least one alkylene glycol ester comprises at least 50% by weight of at least one propylene glycol monocaprylate, preferably at least 60% by weight of at least one propylene glycol monocaprylate, more preferably at least 70% by weight of at least one propylene glycol monocaprylate, based on the total weight of the at least one alkylene glycol ester.

In one embodiment, the at least one propylene glycol monocaprylate is selected from octanoic acid-2-hydroxy-1-methylethyl ester, 2-hydroxylpropyl caprylate, and a combination thereof; and/or the propylene glycol dicaprylate is 1,2-propylene glycol dicaprylate.

In one embodiment, the at least one alkylene glycol ester comprises a mixture of octanoic acid-2-hydroxy-1-methylethyl ester, 2-hydroxylpropyl caprylate, and 1,2-propylene glycol dicaprylate. In one embodiment, the phenoxyethanol and the mixture of octanoic acid-2-hydroxy-1-methylethyl ester, 2-hydroxylpropyl caprylate and 1,2-propylene glycol dicaprylate are comprised in the preservative composition at a weight ratio of from 1:1 to 2:1, preferably at a weight ratio of from 1.2:1 to 1.8:1, and more preferably at a weight ratio of from 1.4:1 to 1.6:1.

In one embodiment, the preservative composition of the present invention comprises (i) phenoxyethanol; and (ii) a mixture of octanoic acid-2-hydroxy-1-methylethyl ester, 2-hydroxylpropyl caprylate and 1,2-propylene glycol dicaprylate; wherein the phenoxyethanol and the mixture of octanoic acid-2-hydroxy-1-methylethyl ester, 2-hydroxylpropyl caprylate and 1,2-propylene glycol dicaprylate are comprised in the preservative composition at a weight ratio of from 1:1 to 2:1, preferably at a weight ratio of from 1.2:1 to 1.8:1, and more preferably at a weight ratio of from 1.4:1 to 1.6:1.

In one embodiment, the preservative composition of the present invention comprises (i) from 45 wt.-% to 70 wt.-% preservative agent, wherein the preservative agent comprises phenoxyethanol; and (ii) from 25 wt.-% to 50 wt.-% of at least one alkylene glycol ester derived from (a) an alkylene glycol, and (b) a fatty acid having from about 6 to 14 carbon atoms; wherein the amounts are based on the total weight of the preservative composition.

In one embodiment, the preservative composition of the present invention comprises (i) from 45 wt.-% to 70 wt.-% phenoxyethanol; and (ii) from 25 wt.-% to 50 wt.-% of a mixture of octanoic acid-2-hydroxy-1-methylethyl ester, 2-hydroxylpropyl caprylate and 1,2-propylene glycol dicaprylate; based on the total weight of the preservative composition.

In a further aspect, the present invention provides a personal care product comprising the preservative composition according to the present invention. In one embodiment, the at least one alkylene glycol ester comprised in the preservative composition is present in the personal care product in an amount of from 1 wt.-% or less, such as in an amount of 0.5 wt.-% or less, based on the weight of the personal care product.

In a further aspect, the present invention provides an end-use formulation comprising the preservative composition according to the present invention.

In a further aspect, the present invention provides the use of the preservative composition according to the present invention for increasing the efficacy against microorganisms compared to an equal amount of the preservative agent without the at least one alkylene glycol ester. In one embodiment, the efficacy is increased by at least 0.5 log reduction. In one embodiment, the efficacy is increased by at least 1.0 log reduction.

In a further aspect, the present invention provides a method for preventing a personal care product from spoilage by microorganisms, the method comprising adding the preservative composition according to the present invention to the personal care product.

In a further aspect, the present invention provides a method for increasing the efficacy of a preservative agent against microorganisms in an end-use formulation, said method comprising providing an end-use formulation and a preservative agent, adding an effective amount of an at least one alkylene glycol ester to the preservative agent and end use formulation to increase the efficacy of the preservative agent in the end-use formulation, as compared to an equal amount of preservative agent without the at least one alkylene glycol ester in the end-use formulation, wherein the preservative agent is selected from the group consisting of phenoxyethanol, bis (3-aminopropyl) dodecylamine, didecyl dimethyl ammonium chloride, sodium benzoate, lactic acid, benzyl alcohol, benzisothiazolinone, sorbic acid, and dehydroacetic acid, or a salt thereof; and wherein the at least one alkylene glycol ester is derived from (a) an alkylene glycol, and (b) a fatty acid having from about 6 to 14 carbon atoms. In one embodiment, the method increases the efficacy of the preservative agent in the end-use formulation by at least 0.5 log reduction, preferably by at least 1.0 log reduction.

These and other aspects will become apparent upon review of the detailed description provided herein.

DETAILED DESCRIPTION

It is to be understood by one of ordinary skill in the art that the present discussion is a description of exemplary embodiments only and is not intended as limiting the broader aspects of the present invention. It is further to be understood that all embodiments and definitions provided herein in the context of the preservative composition are intended to likewise define all other aspects of the present invention such as the inventive formulations, products, methods and uses.

In general, the present invention is directed to a preservative composition. As used herein, the term "preservative" means a biocidal agent or biocidal composition which is intended to be blended with into an end-use formulation, such as personal care formulations, cosmetics, home care formulations, and health and hygiene products, to prevent microorganisms from destroying the end-use formulation or making the end-use formulation unusable for the particular purpose for which the end-use formulation was developed.

It has now been surprisingly found that adding an amount of an alkylene glycol ester to a preservative intended for an end-use formulation can provide an effectively preserved end-use formulation with a synergistic interaction between the preservative and the alkylene glycol ester. As used herein, a "synergistic interaction" refers to the fact that the preservative, when combined with the alkylene glycol ester has a total antimicrobial/antifungal effect that is greater than the antimicrobial/antifungal properties of the preservative alone, or the alkylene glycol ester alone. In other words, the preservative of the present invention operates synergistically with the alkylene glycol ester so as to have greater antimicrobial/antifungal activity in the presence of each against certain microorganisms than in comparison to the antimicrobial activity of the preservative alone or the antimicrobial activity of the alkylene glycol ester alone at the same concentrations. Due to the synergistic effect, the amount of the preservative present in the preservative composition can be reduced while still producing the desired efficacy. This effect is also known as "potentiation" of the preservative agent in the preservative composition. This potentiation of the preservative agent is also referred to herein as a "synergistic effect" between the preservative agent and the alkylene glycol ester(s) for boosting the efficacy of the preservative agent.

Further, use of the preservative composition disclosed herein provide numerous technical advantages and benefits. For example, the preservative composition(s) disclosed herein maintains broad-spectrum activity against all types of microorganisms at various pH levels. Furthermore, the preservative composition(s) disclosed herein generally remain stable during changes in temperature and changes encountered during manufacturing, packaging, shipping, and storage of the end-formulation in which the preservative composition may be included. Further, the preservative composition(s) disclosed herein are physically and chemically compatible with ingredients present in various end-use formulations. Lastly, as described further herein, the preservative composition(s) of the present invention may contain lesser amounts of a preservative agent yet still provide antimicrobial efficacy consistent with industry standards.

The compositions of the present invention can include, consist essentially of, or consist of, the components of the present invention as well as other ingredients described herein. As used herein, "consisting essentially of" means that the composition or component may include additional ingredients, but only if the additional ingredients do not materially alter the basic and novel characteristics of the claimed composition or methods.

As used herein, the term "about" modifying the quantity of a substance, ingredient, component, or parameter employed refers to variation in the numerical quantity that can occur, for example, through typical measuring and handling procedures, e.g., liquid handling procedures used for making concentrates or solutions. Furthermore, variation can occur from inadvertent error in measuring procedures, differences in the manufacture, source, or purity of the ingredients employed to carry out the invention. In one embodiment, the term "about" means within 10% of the reported numerical value. In a more specific embodiment, the term "about" means within 5% of the reported numerical value.

Suitable preservative agents usable in the present invention include, for example, acids, esters and their salts, aldehydes, phenolic compounds, sulfites and iron chelator, aromatic alcohols, quaternary ammonium compounds, aldehydes, pyrone compounds, urea compounds, imidazole compounds, isothiazolinones, amines, and combinations thereof.

In one embodiment, the preservative agent may be an acid compound, including both aromatic and non-aromatic acids. Exemplary acids include, for example, benzoic acid, propionic acid, salicylic acid, sorbic acid, formic acid, undec-10-enoic acid, lactic acid, glycolic acid, and citric acid. In addition, salts of these acids may also be used as well as esters of these acids. Examples of salts include sodium benzoate and potassium sorbate. Other salts may also be used. Acid compounds are typically used as preservatives in end-use formulations in amounts of up to about 3% by weight, depending on the particular acid compound. Similar amounts may be used for the esters and salts. In most cases and used, the amount of the acid, ester or salts thereof are used in amounts up about 1% by weight, more typically up to about 0.6% by weight. Mixtures of acids may also be used as the preservative agent.

In another embodiment, the preservative agent may be an aldehyde. Exemplary aldehydes include, for example, formaldehyde and paraformaldehydes. Exemplary aldehyde forming agents include imidazolidine compounds like hydantoins, such as dimethylol dimethyl hydantoin, (DMDMH) and other similar aldehyde forming hydantoins. Depending on the use, the aldehydes may be present in the composition to be preserved in amounts up to 0.3% by weight. Typically, the amount of the aldehydes is up to 0.2% based on the weight of the composition to be preserved. Mixtures of aldehydes may also be used as the preservative agent.

In a further embodiment, the preservative agent may be a phenolic compound. Exemplary phenolic compounds include, for example, paraben compounds, biphenyl-2-ol (o-phenylphenol) or salts thereof, 4-chloro-m-cresol, 5-Chloro-2-(2,4-dichlorophenoxy)phenol (triclosan), 4-Chloro-3,5-dimethylphenol, 4-isopropyl-m-cresol, 2-benzyl-4-chlorophenol, and bromchlorophen. Exemplary paraben compounds include, for example butyl paraben, propyl paraben, ethyl paraben, methyl paraben and salts thereof, including, for example, potassium, sodium and/or calcium salts. Phenolic compounds are typically used as preservatives in end-use formulation in amounts up to about 1% by weight, based on the weight of the total end-use formulation. This upper limit depends on the particular phenolic compound. More typically up to about 0.5% by weight of the phenolic compound is used in cosmetic formulations.

In yet another embodiment, the preservative agent may be a compound which is a known as an iron chelator. Exemplary iron chelators include pyrithione compounds and compounds such as piroctone olamine or hydroxyl pyridine compounds and salts thereof. Pyrithione is known by several names, including 2 mercaptopyridine-N-oxide; 2-pyridinethiol-1-oxide (CAS Registry No. 1 121-31-9); 1-hydroxypyridine-2-thione and 1 hydroxy-2(1H)-pyridinethione (CAS Registry No. 1 121-30-8); 2-pyridinol-1-oxide (HPNO) and N-hydroxy-6-octyloxypyridine 2(1H)-one and -hydroxy-6-octyloxypyridine 2(1H)-one ethanolamine salt. Pyrithione salts are commercially available from Lonza, Inc., such as Sodium OMADINE® or Zinc OMADINE®.

The pyrithione present as the preservative agent can be present in a water insoluble form or in a water-soluble form. The pyrithione may comprise sodium pyrithione, zinc pyrithione, barium pyrithione, strontium pyrithione, copper pyrithione, cadmium pyrithione, and/or zirconium pyrithione. Other pyrithiones that may be present in the composition include sodium pyrithione, bismuth pyrithione, potassium pyrithione, lithium pyrithione, ammonium pyrithione, calcium pyrithione, magnesium pyrithione, silver pyrithione, gold pyrithione, manganese pyrithione, and/or an organic amine pyrithione. A single pyrithione may be present as the preservative agent or a combination of any of the above may be included as the preservative agent.

The pyrithione particles can have a particle size such that 100% of the particles have a particle size of less than about 10 microns and at least 70% of the particles have a particle size less than 5 microns, such as at least about 50% of the particles can have a particle size of 1 micron or less. Particle size can be measured using a laser scattering particle size analyzer, such as a HORIBA LA 910 particle size analyzer.

The pyrithione particles can be produced by reacting pyrithione or a water-soluble salt of pyrithione, and a water-soluble polyvalent metal salt in a pressurized, turbulent flow reactor that generates pulverizing forces. The pulverizing forces produced by the pressurized, turbulent flow reactor efficiently generate pyrithione salt particles of micron size. The micron-sized pyrithione salt particles made by the method have a narrow and uniform size distribution and have excellent surface deposition properties due to the large surface area provided by the population of micron particles.

Iron chelator compounds are typically used as preservatives in end-use formulations in amounts up to about 1% by weight, depending on the particular compound. Of particular interest are zinc pyrithione and piroctone olamine. These iron chelators may also have other advantages, such as providing other benefits, including antidandruff properties.

In another embodiment, the preservative agent may include inorganic sulfite compounds and hydrogen sulfites compounds. Sulfite compound are generally present in amounts up about 0.5% by weight, based on the total weight of the end-use formulation.

In some embodiments, the preservative agent includes alcohol compounds. The alcohol may be a lower alcohol or an aromatic alcohol. Lower alcohols are typically selected among mono-functional low-molecular alcohols, preferably alkanols with one to four carbon atoms such as methanol, ethanol, isopropanol or butanol, or combinations thereof. Substituted alcohols, such a chlorobutanol may also be used. Particularly suitable lower alcohols include ethanol and isopropyl alcohol. Aromatic alcohols may also be used. Suitable aromatic alcohols include phenoxyethanol, 2,4-Dichlorophenyl)methanol, benzyl alcohol, 1-Phenoxypropaneol, chlorphenesin, and benzyl hemiformal. One particularly preferred alcohol is phenoxyethanol. The alcohol compounds may be used as preservative agents in end-use formulations in amounts up to about 1.5% by weight based on the total weight of the end-use formulation, depending on the particular alcohol compound. In most cases, the amount of the alcohol compounds is typically used in amounts up about 1% by weight, more typically up to about 0.5% by weight, based on the weight of the end-use formulation.

In another embodiment, one or more quaternary ammonium compounds may be used as preservative agent. Quaternary ammonium compounds, also known as "quats", typically comprise at least one quaternary ammonium cation with an appropriate anion. Quats will generally have the general formula (1).

(1)

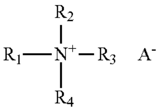

The groups $R_1$, $R_2$, $R_3$ and $R_4$ can vary within wide limits and possess anti-microbial properties. Typically, at least one, such as at least two, of $R_1$, $R_2$, $R_3$ and $R_4$ is a lower alkyl, meaning having 1 to 4 carbon atoms, such as a methyl, ethyl, propyl or butyl group. In one aspect, at least one, such as least two of $R_1$, $R_2$, $R_3$ and $R_4$ is a longer chain alkyl group of 6 to 24 carbon atoms. R4 can also be a substituted or unsubstituted benzyl group such as an ethylbenzyl group, or an alkoxy group. $A^-$ is a monovalent anion or one equivalent of a polyvalent anion of an inorganic or organic acid. Suitable anions for $A^-$ are in principle all inorganic or organic anions, in particular halides, for example chloride or bromide, carbonates, bicarbonates, carboxylates, sulfonates, phosphates, propionates, saccharinates, or a mixture thereof. Carboxylates may be derived from lower carboxylic acids or from fatty acids.

Alkyl, hereinafter, is taken to mean in each case unbranched or branched alkyl groups of the specified number of carbons, but preferably unbranched alkyl groups, and particularly preferably those having an even number of carbon atoms. In particular, this is also taken to mean the homologue mixtures derived from natural raw materials, for example "cocoalkyl".

In one embodiment, the quaternary ammonium compound may have the following R groups: R1, R2 and R3 are alkyl groups and R4 is a benzyl group, a $C_{1-18}$ alkyl group such as a $C_{6-18}$ alkyl group, or an alkoxy group such as a group having the structure $—[(CH_2)_2—O]_nR_5$ where n=1-20 and $R_5$ is hydrogen or an unsubstituted or substituted phenyl, and $A^-$ is as described above, such as a monovalent anion or one equivalent of a polyvalent anion of an inorganic or organic acid. For example, R1 is an alkyl group having 1 to 4 carbon atoms and R2 and R3 are independently alkyl groups having 6 to 24 carbon atoms, or R1 and R2 are independently alkyl groups having 1 to 4 carbon atoms and R3 is an alkyl group having 6 to 24 carbon atoms.

Suitable quaternary ammonium compounds include, for example alkyl ($C_{12-22}$) trimethyl ammonium bromide, alkyl ($C_{12-22}$) trimethyl ammonium chloride compounds including, for example cetrimonium bromide, cetrimonium chloride, laurtrimonium bromide, laurtrimonium chloride, steartrimonium bromide, and steartrimonium chloride or mixture thereof, benzethonium compound, including, for example benzalkonium chloride, benzalkonium bromide and benzalkonium saccharinate.

In one embodiment, the quaternary ammonium compound may comprise a dialkyl ammonium compound, such as a dimethyl dialkyl ammonium compound. In one embodiment, the dimethyl dialkyl ammonium compound may have between about 8 and about 12 carbon atoms, such as from about 8 to about 10 carbon atoms in each of the alkyl groups.

Examples of dimethyl dialkyl ammonium compounds include dimethyl dioctyl ammonium compounds such as dimethyl dioctyl ammonium chloride, dimethyl didecyl ammonium compounds such as dimethyl didecyl ammonium chloride and the like. Mixtures of dimethyl dialkyl ammonium compounds may also be used, and other anions, such as those described above, may also be used. Commercially available dimethyl dialkyl ammonium compounds include, for example, compositions marketed and sold under the BARDAC®, BARDAP®, BARQUAT®, or CARBOQUAT® trade names by Lonza Inc.

Such commercially available examples of dimethyl dialkyl ammonium compounds include dioctyldimethylammonium chloride (available as Bardac® LF and LF-80 from Lonza, Inc.), octyldecyldimethylammonium chloride (available as a mixture of octyldecyldimethylammonium chloride, dioctyldimethylammonium chloride, and didecyldimethyl ammonium chloride as Bardac® 2050 and 2080 from Lonza, Inc.), didecyldimethylammonium chloride (available as Bardac® 2250 and 2280 from Lonza, Inc.), decylisononyldimethylammonium chloride (available as Bardac® 21 from Lonza, Inc.), diisodecyldimethylammonium chloride (available as BTC 99 from Stepan Co. of Northfield, Ill.), and any combination of any of the foregoing.

The quaternary ammonium compounds may be included in end-use formulations in amounts up to about 0.2% by weight based on the total weight of the end-use formulation, depending on the particular quaternary ammonium compound. In certain embodiments, the end-use formulation may contain from about 0.1% by weight to about 0.05% by weight, based on the weight of the end-use formulation.

Exemplary pyrone compounds useable in the present invention as a preservative agent include, for example, dehydroacetic acid and salts thereof. Pyrone compounds may be used in amount up to about 1.0% by weight, based on the total weight of the end-use formulation. In some embodiments, one or more pyrone compounds may be used in an amount of up to about 0.6% by weight.

In some embodiments, the preservative agent may include one or more isothiazolinones. Exemplary isothiazolinones include, for example 5-chloro-2-methyl-isothiazol-3-one (chloromethylisothiazolinone), 2-methyl-isothiazol-3-one (methylisothiazolinone), benzisothiazolinone and mixtures thereof. In certain embodiments, one or more isothizaolinones may be used in an amount of up to about 0.01% by weight of the end-use formulation.

One more urea compounds may be used as the preservative agent in certain embodiments, Exemplary urea compounds include, for example, 3-(4-Chlorophenyl)-1-(3,4-dichlorophenyl)urea (triclocarban); 1,1'-methylenebis{3-[4-(hydroxymethyl)-2,5-dioxoimidazolidin-4-yl]urea}; and N-(hydroxymethyl)-N-(dihydroxymethyl-1,3-dioxo 2,5-imidazolinidyl-4)-N'-(hydroxymethyl) urea. These compounds are typically used in amounts up to about 0.5% by weight of the end-use formulation.

Exemplary imidazole compounds useable in the present invention as the preservative agent include, for example, 1-(4-chlorophenoxy)-1-(imidazole-1-yl)-3,3-dimethylbutan-2-one); 1,3-Bis(hydroxymethyl)-5,5-dimethylimidazolidine-2,4-dione). In some embodiments, one or more urea compounds may be included in an amount of up to about 0.5% by weight of the end-use formulation.

In still another aspect, the preservative agent can be an amine compound, such as a triamine compound. Suitable triamine compounds include, but are not limited to, those having the formula

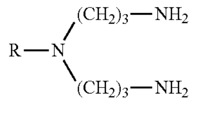

where R is a substituted or unsubstituted $C_8$ to $C_{18}$alkyl, $C_8$ to $C_{18}$ alkenyl, $C_8$ to $C_{18}$ alkynyl, or $C_8$ to $C_{18}$ cycloalkyl or aryl, and R is optionally interrupted with one or more heteroatoms.

The term "substituted" as used herein includes compounds substituted with one or more of halogen (such as F, Cl, 1, or Br); heteroatomic groups; $C_8$ to $C_{18}$ alkyl; $C_8$ to $C_{18}$ alkenyl; $C_8$ to $C_{18}$ alkynyl; $C_8$ to $C_{18}$ cycloalkyl; aryl; or carbonyl containing $C_8$ to $C_{18}$ alkyl, $C_8$ to $C_{18}$ alkenyl, or $C_8$ to $C_{18}$ alkynyl groups (such as ketones, esters, ethers, carbonates, or carboxylates).

Suitable heteroatoms include, but are not limited to, O, N, P, and S.

Suitable heteroatomic groups include, but are not limited to, $—NH_2$, $—NO_2$, $—SO_2$, $—SO_3$, $—PO_3$, $=O$, and —OH.

The substituent R is preferably unsubstituted $C_8$ to $C_{18}$ alkyl, $C_8$ to $C_{18}$ alkenyl, $C_8$ to $C_{18}$ alkynyl, $C_8$ to $C_{18}$ cycloalkyl, or aryl. Preferred triamines include, but are not limited to, N,N-bis(3-aminopropyl)-dodecylamine, available as Lonzabac® 12 from Lonza Inc. of Fair Lawn, N.J., bis(3-aminopropyl)octylamine, and N,N-bis(3-aminopropyl)-octylamine.

The amine preservative agent can generally be included in an amount up to about 2% by weight of the end use formulation, and particularly from about 50 ppm to about 200,000 ppm, such as from about 50 ppm to about 500 ppm.

Other components that may be used as a preservative agent include dibromohexamidine and salts thereof; thiomersal; phyenylmercuric salts; hexetidine; 2-bromo-2-nitropropane-1,3-diol; 5-bromo-5-nitro-1,3-dioxane; polyhexamethylenebiguanide or salts thereof; hexamethylenetetramine; methenamine 3-chloroallylochloride; 2-chloroacetamide; chlorohexidine and its digluconoate, or diacetate esters and dihydrochloride salt thereof; 4,4-dimethyl, 1,3-oxazolidine; glutaraldehyde; 5-ethyl-3,7-dioxa-1-azabicyclo octane; Sodium hydroxymethylglycinate, 3-Iodo-2-propynyl butylcarbamate (IPBC) and ethyl lauroyl alginate. In certain embodiments, these components may be included in an amount of up to about 0.5% by weight of the end-use formulation.

In addition, the preservative agent may be a single preservative agent, a mixture of two or more preservative agents from a single type of preservative agent or may be a mixture of two or more different types of preservative agents.

Embodiments of the present invention include one or more alkylene glycol esters. Alkylene glycol esters useable in the present invention may be formed from saturated, unsaturated, natural or synthetic fatty acids, and the like. For instance, saturated fatty acids include caprylic acid, capric acid, hexanoic acid, dodecanoic acid, lauric acid, myristic acid, palmitic acid, stearic acid, arachidic acid, behenic acid, lignoceric acid, cerotic acid, combinations thereof, derivatives thereof, and the like. Fatty acids having a carbon chain length of from about 5 carbon atoms to about 16 carbon atoms are well suited for use in forming the alkylene glycol ester. The alkylene glycol ester can be formed from any suitable alkylene, such as ethylene, butylene or propylene. The alkylene glycol ester can comprise a monoester or a diester. In one aspect, a mixture of monoesters, a mixture of diesters, or a mixture of monoesters and diesters may be incorporated into the composition of the present invention. In one aspect, at least one monoester is utilized and comprises the majority of the alkylene glycol ester present.

In some embodiments, the alkylene glycol ester(s) is derived from (a) a propylene glycol, ethylene glycol, or butylene glycol component, and (b) a fatty acid having from about 6 to 12 carbon atoms, such as caproic acid, caprylic acid, capric acid, lauric acid, and mixtures of the like. For example, propylene glycol C6-C12 fatty acid monoesters or diesters may be used. Propylene glycol C6-C14 fatty acid monoesters or diesters may also be used.

Suitable examples of alkylene glycol esters, include but are not limited to, propylene glycol isostearate, propylene glycol laurate, propylene glycol myristate, propylene glycol oleate, propylene glycol monolaurate, propylene glycol monocaprate, propylene glycol monocaprylate, propylene glycol monocaproate, propylene glycol diperlargonate, propylene glycol diisostearate, propylene glycol dilaurate, propylene glycol monopalmitate, propylene glycol monostearate, ethylene glycol isostearate, ethylene glycol laurate, ethylene glycol myristate, ethylene glycol oleate, ethylene glycol monolaurate, ethylene glycol monocaprate, ethylene glycol monocaprylate, ethylene glycol monocaproate, ethylene glycol diperlargonate, ethylene glycol diisostearate, ethylene glycol dilaurate, ethylene glycol monopalmitate, ethylene glycol monostearate, butylene glycol isostearate, butylene glycol laurate, butylene glycol myristate, butylene glycol oleate, butylene glycol monolaurate, butylene glycol monocaprate, butylene glycol monocaprylate, butylene glycol monocaproate, butylene glycol diperlargonate, butylene glycol diisostearate, butylene glycol dilaurate, butylene glycol monopalmitate, butylene glycol monostearate, or mixtures thereof, other complexes or derivatives thereof, and the like.

A suitable example of an alkylene glycol diester is propylene glycol dicaprylate.

In one aspect, the alkylene glycol ester is primarily propylene glycol monocaprylate. The propylene glycol monocaprylate product can include a mixture of propylene glycol monoesters and diesters. For example, the product may contain 2-hydroxylpropyl caprylate (40 to 70 wt %), octanoic acid-2-hydroxy-1-methylethyl ester (23 to 33 wt %), and 1,2-propylene glycol dicaprylate (5 to 28 wt %).

In one embodiment, the alkylene glycol ester comprises propylene glycol caprylate. In one embodiment, the alkylene glycol ester comprises a mixture of at least one propylene glycol monocaprylate and propylene glycol dicaprylate. In one embodiment, the alkylene glycol ester is of a mixture of at least one propylene glycol monocaprylate and propylene glycol dicaprylate. In one embodiment, the at least one propylene glycol monocaprylate is selected from octanoic acid-2-hydroxy-1-methylethyl ester, 2-hydroxylpropyl caprylate, and a combination thereof. In one embodiment, the at least one propylene glycol monocaprylate is a mixture of octanoic acid-2-hydroxy-1-methylethyl ester and 2-hydroxylpropyl caprylate. In one embodiment, the propylene glycol dicaprylate is 1,2-Propylene glycol dicaprylate. In one embodiment, the alkylene glycol ester comprises at least 50% by weight of at least one propylene glycol monocaprylate, preferably at least 60% by weight of at least one propylene glycol monocaprylate, more preferably at least 70% by weight of at least one propylene glycol monocaprylate, based on the total weight of the alkylene glycol ester. In one embodiment, the at least one propylene glycol monocaprylate and the propylene glycol dicaprylate are comprised in the mixture at a weight ratio of from 15:1 to 1:1, preferably at a weight ratio of from 10:1 to 1:1, more preferably at a weight ratio of from 5:1 to 2:1.

In one embodiment, the alkylene glycol ester comprises a mixture of octanoic acid-2-hydroxy-1-methylethyl ester, 2-hydroxylpropyl caprylate, and 1,2-propylene glycol dicaprylate. In one embodiment, the alkylene glycol ester comprises from 20 wt.-% to 35 wt.-% octanoic acid-2-hydroxy-1-methylethyl ester, from 40 wt.-% to 70 wt.-% 2-hydroxylpropyl caprylate, and from 5 wt.-% to 30 wt.-% 1,2-propylene glycol dicaprylate, based on the total weight of the alkylene glycol ester.

In one embodiment, the alkylene glycol ester comprises from 20 wt.-% to 30 wt.-% octanoic acid-2-hydroxy-1-methylethyl ester, from 40 wt.-% to 60 wt.-% 2-hydroxylpropyl caprylate, and from 20 wt.-% to 30 wt.-% 1,2-propylene glycol dicaprylate, based on the total weight of the alkylene glycol ester.

In one embodiment, the alkylene glycol ester comprises from 20 wt.-% to 40 wt.-% octanoic acid-2-hydroxy-1-methylethyl ester, from 50 wt.-% to 70 wt.-% 2-hydroxylpropyl caprylate, and from 5 wt.-% to 15 wt.-% 1,2-propylene glycol dicaprylate, based on the total weight of the alkylene glycol ester.

In some embodiments, the alkylene glycol ester may not include a propylene glycol monoester derived from a propylene glycol component and a fatty acid having equal to or more than 16, carbons such as palmitic acid. While not being bound by any particular theory, it has been discovered that the combination of a preservative agent and a propylene glycol monoester containing C16 fatty acid, may not provide additive or synergistic benefits. Accordingly, in certain embodiments, the alkylene glycol ester utilized in the compositions described herein may be substantially free of a propylene glycol monoester containing a C16 fatty acid, such as palmitic acid.

The weight ratio of the at least one alkylene glycol ester to the preservative agent (PA) can vary depending on a variety of factors. For example, the weight ratio of the at least one alkylene glycol ester to the preservative agent can depend on the composition of the final product, the microorganisms that are being controlled, the particular alkylene glycol ester and preservative agent used, the final properties of the product, and the like. The weight ratio of the at least one alkylene glycol ester to the preservative agent, for instance, can be in the range of about 1:50,000 to about 500:1, such as from about 1:10,000 to about 300:1, such as from about 1:5,000 to about 10:1, such as from about 1:2,500 to about 8:1, such as from about 1:1,500 to about 2:1. In many applications, only a small amount of alkylene glycol ester is needed in order to enhance the efficacy of the preservative agent. For example, in one aspect, the preservative agent is present in greater amounts than the at least one alkylene glycol ester. In certain embodiments, the weight ratio of the alkylene glycol ester to the preservative agent can be from about 1:5,000 to about 4:1, such as from about 1:1,500 to about 4:1, such as from about 1:300 to about 4:1, such as from about 1:20 to about 4:1, such as from about 1:15 to about 4:1, such as from about 1:10 to about 4:1. In one embodiment, the preservative agent and the at least one alkylene glycol ester are comprised in the preservative composition at a weight ratio of from 1:1 to 6:1. In one embodiment, the preservative agent and the at least one alkylene glycol ester are comprised in the preservative composition at a weight ratio of from 1.1:1 to 3:1. In one embodiment, the preservative agent and the at least one alkylene glycol ester are comprised in the preservative composition at a weight ratio of from 1.2:1 to 2:1.

In one embodiment, the preservative agent is phenoxyethanol and preferably the phenoxyethanol and the at least one alkylene glycol ester are comprised in the preservative composition at a weight ratio of from 6:1 to 1:1, preferably of from 3:1 to 1:1, more preferably of from 2:1 to 1:1.

In one embodiment, the preservative agent is bis (3-aminopropyl) dodecylamine and preferably the bis (3-aminopropyl) dodecylamine and the at least one alkylene glycol ester are comprised in the preservative composition at a weight ratio of from 25:1 to 1:25, preferably of from 20:1 to 1:20, more preferably of from 15:1 to 1:15.

In one embodiment, the preservative agent is didecyl dimethyl ammonium chloride and preferably the didecyl dimethyl ammonium chloride and the at least one alkylene glycol ester are comprised in the preservative composition at a weight ratio of from 25:1 to 1:25, preferably of from 20:1 to 1:20, more preferably of from 15:1 to 1:15.

In one embodiment, the preservative agent is sodium benzoate and preferably the sodium benzoate and the at least one alkylene glycol ester are comprised in the preservative composition at a weight ratio of from 50,000:1 to 50:1, preferably of from 10,000:1 to 100:1, more preferably of from 5000:1 to 150:1.

In one embodiment, the preservative agent is lactic acid and preferably the lactic acid and the at least one alkylene glycol ester are comprised in the preservative composition at a weight ratio of from 250:1 to 1:1, preferably of from 220:1 to 1:1, more preferably of from 200:1 to 2:1.

In one embodiment, the preservative agent is benzyl alcohol and preferably the benzyl alcohol and the at least one alkylene glycol ester are comprised in the preservative composition at a weight ratio of from 800:1 to 1:1, preferably of from 600:1 to 2:1, more preferably of from 400:1 to 3:1.

In one embodiment, the preservative agent is benzisothiazolinone and preferably the benzisothiazolinone and the at least one alkylene glycol ester are comprised in the preservative composition at a weight ratio of from 40:1 to 1:4, preferably of from 60:1 to 1:3, more preferably of from 40:1 to 1:2.

In one embodiment, the preservative agent is sorbic acid and preferably the sorbic acid and the at least one alkylene glycol ester are comprised in the preservative composition at a weight ratio of from 100:1 to 1:4, preferably of from 80:1 to 1:3, more preferably of from 60:1 to 1:2.

In one embodiment, the preservative agent is dehydroacetic acid and preferably the dehydroacetic acid and the at least one alkylene glycol ester are comprised in the preservative composition at a weight ratio of from 1000:1 to 10:1, preferably of from 800:1 to 15:1, more preferably of from 600:1 to 20:1.

In one embodiment, the at least one alkylene glycol ester comprises a mixture of at least one propylene glycol monocaprylate and propylene glycol dicaprylate. In one embodiment, the at least one alkylene glycol ester comprises at least 50% by weight of at least one propylene glycol monocaprylate, preferably at least 60% by weight of at least one propylene glycol monocaprylate, more preferably at least 70% by weight of at least one propylene glycol monocaprylate, based on the total weight of the alkylene glycol ester. In one embodiment, the at least one propylene glycol monocaprylate and the propylene glycol dicaprylate are comprised in the mixture at a weight ratio of from 15:1 to 1:1, preferably at a weight ratio of from 10:1 to 1:1, more preferably at a weight ratio of from 5:1 to 2:1. In one embodiment, the phenoxyethanol and the mixture of the at least propylene glycol monocaprylate and propylene glycol dicaprylate are comprised in the preservative composition at a weight ratio of from 6:1 to 1:1, preferably of from 3:1 to 1:1, more preferably of from 2:1 to 1:1. In one embodiment, the phenoxyethanol and the mixture of the at least propylene glycol monocaprylate and propylene glycol dicaprylate are comprised in the preservative composition at a weight ratio of from 1:1 to 2:1, preferably at a weight ratio of from 1.2:1 to 1.8:1, and more preferably at a weight ratio of from 1.4:1 to 1.6:1.

In one embodiment, the alkylene glycol ester comprises a mixture of octanoic acid-2-hydroxy-1-methylethyl ester, 2-hydroxylpropyl caprylate, and 1,2-propylene glycol dicaprylate and the preservative agent comprises phenoxyethanol. In one embodiment, the phenoxyethanol and the mixture of octanoic acid-2-hydroxy-1-methylethyl ester, 2-hydroxylpropyl caprylate and 1,2-propylene glycol dicaprylate are comprised in the preservative composition at a weight ratio of from 1:1 to 2:1, preferably at a weight ratio of from 1.2:1 to 1.8:1, and more preferably at a weight ratio of from 1.4:1 to 1.6:1.

In one embodiment, the preservative composition comprises (i) phenoxyethanol; and (ii) a mixture of octanoic acid-2-hydroxy-1-methylethyl ester, 2-hydroxylpropyl caprylate, and 1,2-propylene glycol dicaprylate.

In one embodiment, the preservative composition comprises (i) phenoxyethanol; and (ii) a mixture of octanoic acid-2-hydroxy-1-methylethyl ester, 2-hydroxylpropyl caprylate, and 1,2-propylene glycol dicaprylate, wherein the phenoxyethanol and the mixture of octanoic acid-2-hydroxy-1-methylethyl ester, 2-hydroxylpropyl caprylate and 1,2-propylene glycol dicaprylate are comprised in the preservative composition at a weight ratio of from 1:1 to 2:1, preferably at a weight ratio of from 1.2:1 to 1.8:1, and more preferably at a weight ratio of from 1.4:1 to 1.6:1.

In one embodiment, the preservative comprises (i) from 45 wt.-% to 70 wt.-% preservative agent, wherein the preservative agent comprises phenoxyethanol; and (ii) from 25 wt.-% to 50 wt.-% of at least one alkylene glycol ester derived from (a) an alkylene glycol, and (b) a fatty acid having from about 6 to 14 carbon atoms; wherein the amounts are based on the total weight of the preservative composition.

In one embodiment, the preservative composition comprises (i) from 45 wt.-% to 70 wt.-% phenoxyethanol; and (ii) from 25 wt.-% to 50 wt.-% of a mixture of octanoic acid-2-hydroxy-1-methylethyl ester, 2-hydroxylpropyl caprylate and 1,2-propylene glycol dicaprylate; wherein the amounts are based on the total weight of the preservative composition.

The present invention further pertains to an end-use formulation comprising the preservative composition according to the present invention. The amount of the preservative agent used in the end-use formulation of the present invention varies, as described above, depending on the particular preservative agents. In an alternative embodiment, the preservative agent may be formulated in the form of a preservative concentrate. By "preservative concentrate" or "preservative composition" it is meant a composition which is to be added to an end-use formulation in a specified amount. In the preservative concentrate, the amount of the preservative agent will be higher than final use amounts formulated in end-use products. In certain embodiments, the preservative concentrate may contain only the preservative agent and the at least one alkylene glycol ester. Alternatively, in certain embodiments, the preservative concentrate may contain the preservative agent, the at least one alkylene glycol ester and a carrier that is compatible with end-use formulations. Exemplary carriers include, for example, water, an aqueous solvent or other solvents acceptable for end-use formulations and uses of these formulations. The preservative concentrate can be added to end-use formulation in an amount necessary to achieve the desired amount of the preservative in the final end-use formulation.

When contained in a preservative concentrate, the preservative agent and the at least one alkylene glycol ester may be combined with various different components. For instance, in one embodiment, the preservative concentrate may contain a solvent. The solvent can be a polar solvent such as water, or a water-miscible solvent, such as an alcohol and/or a glycol ether. In certain embodiments, the anti-microbial composition can further include a water-miscible organic solvent. Examples of suitable water-miscible solvents include ethanol, propanol, benzyl alcohol, isopropanol, diethylene glycol propyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monobutyl ether, diethylene glycol monoethyl ether, diethylene glycol mono-n-butyl ether, ethylene glycol dimethyl ether, ethylene glycol diethyl ether, ethylene glycol dibutyl ether, propylene glycol n-butyl ether, tripropylene glycol methyl ether, dipropylene glycol methyl ether, dipropylene glycol butyl ether and combinations thereof.

In other embodiments, one or more alkylene glycol esters and the preservative agent may be added to an end-use formulation independent of each other. For example, in certain embodiments the at least one alkylene glycol ester may be added to the preservative agent prior to the addition of the preservative agent to the end-use formulation. Still in some embodiments, the at least one alkylene glycol ester may be added to end-use formulation after the preservative agent is added to the end-use formulation. In some embodiments, the at least one alkylene glycol ester may be added to the end-use formulation prior to the addition of the preservative agent to the end-use formulation. In certain embodiments, the at least one alkylene glycol ester may be added concurrently with the preservative agent to the end-use formulation as separate ingredients.

The present invention further pertains to the use of the preservative composition according to the present invention for increasing the efficacy against microorganisms compared to an equal amount of the preservative agent without the at least one alkylene glycol ester. In one embodiment, the efficacy is increased by at least 0.5 log reduction. In one embodiment, the efficacy is increased by at least 1.0 log reduction.

The present invention further pertains to a personal care product comprising the preservative composition according to the present invention. In one embodiment, the at least one alkylene glycol ester comprised in the preservative composition is present in the personal care product in an amount of from 1 wt.-% or less, such as in an amount of 0.5 wt.-% or less, based on the weight of the personal care product.

The present invention further pertains to a method for preventing a personal care product from spoilage by microorganisms, the method comprising adding the preservative composition according to the present invention to the personal care product.

The present invention further pertains to a method for increasing the efficacy of a preservative agent against microorganisms in an end-use formulation, said method comprising providing an end-use formulation and a preservative agent, adding an effective amount of at least one alkylene glycol ester to the preservative agent and end use formulation to increase the efficacy of the preservative agent in the end-use formulation, as compared to an equal amount of preservative agent without the at least one alkylene glycol ester in the end-use formulation, wherein the preservative agent and the at least one alkylene glycol ester are defined as for the inventive preservative composition.

Various different microorganisms may be controlled in accordance with the present invention. For instance, the preservative composition of the present invention can control gram positive bacteria, gram negative bacteria, and the like. In addition to bacteria, the preservative composition of the present invention can also kill and control the growth of various other microorganisms, such as fungi, viruses, spores, yeast, mycobacteria, and the like. Non-limiting examples of particular microorganisms that may be controlled in accordance with the present invention include *Staphylococcus aureus, Streptococcus pneumoniae, Pseudomonas aeruginosa, Serratia marcescens, Salmonella enteritidis, Neisseria gonorrhoeae, Escherichia coli, Enterococcus hirae, Acinetobacter baumannii, Listeria monocytogenes, Enterobacter gergoviae, Klebsiella pneumoniae, Burkholderia cepacia, Pseudomonas putida, Kocuria rhizophila, Candida albicans, Saccharomyces cerevisiae, Aspergillus brasiliensis, Penicillium funiculosum, Eupenicillium levitum, Bacillus cereus, Bacillus subtilis, Clostridium difficile, Clostridium perfringens, Mycobacterium tuberculosis, Mycobacterium terrae, Mycobacterium avium*, Poliovirus, Adenovirus, Norovirus, Vaccinia virus, Influenza virus, Hepatitis B virus, Human Immunodeficiency virus, Human papilloma virus, or mixtures thereof.

In general, the preservative composition of the present invention can be incorporated into any number of different end-use formulations or products. As used herein, "end-use formulations" or "end-use products" is intended to mean personal care products, including cosmetics, home care products, and health and hygiene products. For instance, personal care products may include products such as cosmetic formulations, including face creams, makeup removers, mascaras or wet wipes. The personal care product formulation also includes shampoos, conditioners, skin lotions or liquids for any personal care wet wipe application. The personal care product formulation can include any product for topical application to a user's skin or hair. When the preservative compositions disclosed herein are formulated into a personal care product, the preservative composition provides effective, broad spectrum preservation activity over a broad pH range. For instance, in certain embodiments, the personal care product may have a pH ranging from about 2 to 9, such as from about 3 to about 8, particularly from about 3 to about 6. Accordingly, the preservative composition disclosed herein may exhibit broad antimicrobial coverage for the end-use product across a range of end-use products having a spectrum of pHs.

In certain embodiments, the preservative composition disclosed herein may have a pH of from about 2 to about 9, such as from about 3 to about 8, particularly from about 3 to about 6.

The personal care product formulation may comprise a base formulation to which the preservative composition of the present invention is added. The base formulation may contain numerous and different ingredients depending upon the end use application. The personal care product formulation, for instance, may contain solvents, surfactants, emulsifiers, consistency factors, conditioners, emollients, skin caring ingredients, moisturizers, thickeners, humectants, fillers, anti-oxidants, other preservatives, active ingredients, in particular dermatologically active ingredients, fragrances and the like, as well as mixtures thereof. Active ingredients as mentioned herein comprise, for example, anti-inflammatories, anti-bacterials, anti-fungals and the like agents. Active ingredients suited for topical applications are particularly preferred.

Suitable surfactants comprise: alkyl sulfates e.g. sodium lauryl sulfate, ammonium lauryl sulfate; sodium cetearyl sulfate; alkyl sulfoacetates e.g. sodium lauryl sulfoacetate; alkyl ether sulfates e.g. sodium laureth sulfate; sodium trideceth sulfate; sodium oleth sulfate; ammonium laureth sulfate; alkyl ether sulfosuccinates e.g. disodium laureth sulfosuccinate; alkyl glycosides e.g. decyl glucoside; lauryl glucoside; alkyl isethionates amphoterics e.g. cocamidopropyl betaine; sodium cocoamphoacetate; sodium lauroamphoacetate; disodium lauroamphodiacetate; disodium cocoamphodiacetate; sodium lauroamphopripionate; disodium lauroamphodipropionate; potassium or ammonium salts of the aforementioned amphoterics; capryl/capramidopropyl betaine; undecylenamidopropyl betaine; lauromidopropyl betaine; and fatty alcohol polyglycol ethers.

Suitable emulsifiers include e.g. anionics as salts of fatty acids e.g. sodium stearate or sodium palmitate, organic soaps e.g. mono-, di- or triethanolaminoeate, sulfated or sulfonated compounds e.g. sodium lauryl sulfate or sodium cetyl sulfonate, saponines, lamepones; cationics as quaternary ammonium salts; nonionics as fatty alcohols, fatty acid ester with saturated or unsaturated fatty acids, polyoxyethylenesters or polyoxyethylenethers of fatty acids, polymers from ethylene oxide and propylene oxide or propylene glycol, amphotherics as phosphatides, proteins as gelatine, casein alkylamidobetaines, alkyl betaines and amphoglycinates, alkyl phosphates, alkylpolyoxyethylene phosphates or the corresponding acids, silicone derivatives, e.g. alkyl dimethiconecoplyol.

Suitable consistency factors include e.g. fatty alcohols or their mixtures with fatty acid esters, e.g. acetylated lanolin alcohol, aluminum stearates, carbomer, cetyl alcohol, glyceryl oleate, glyceryl stearate, glyceryl stearate (and) PEG 100 stearate, magnesium stearate, magnesium sulfate, oleic acid, stearic acid, stearyl alcohol, myristyl myristate, isopropyl palmitate, beeswax and synthetic equivalents thereof, carbomers, and the like. Suitable conditioners are e.g. alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, quaternized protein hydrolysates, quaternized cellulose and starch derivatives, quaternized copolymers of acrylic or methacrylic acid or salts, quaternized silicone derivatives.

Suitable emollients include e.g. cetearyl isononanoate, cetearyl octanoate, decyl oleate, isooctyl stearate, coco caprylate/caprate, ethylhexyl hydroxystearate, ethylhexyl isononanoate, isopropyl isostearate, isopropyl myristate, oleyl oleate, hexyl laurate, paraffinum liquidum, PEG-75 lanolin, PEG-7 glyceryl cocoate, petrolatum, ozokerite cyclomethicone, dimethicone, dimethicone copolyol, dicaprylyl ether, *Butyrospermum parkii, Buxus chinensis*, canola, carnauba cera, *Copernicia cerifera, Oenothera biennis, Elaeis guineensis, Prunus dulcis*, squalane, *Zea mays, Glycine soja, Helianthus annuus*, lanolin, hydrogenated castor oil, hydrogenated coconut oil, hydrogenated polyisobutene, sucrose cocoate, stearoxy dimethicone, lanolin alcohol, isohexadecane.

Suitable skin care ingredients include e.g. plant extracts, bisabolol, anti-inflammatory agents, urea, allantoin, panthenol and panthenol derivatives, phytantriol, vitamins A, E, C, D, ceramides of animal or plant origin, lecithins, and the like.

Suitable moisturizers include e.g. butylenes glycol, cetyl alcohol, dimethicone, dimyristyl tartrate, glucose glycereth-26, glycerin, glyceryl stearate, hydrolyzed milk protein, lactic acid, lactose and other sugars, laureth-8, lecithin, octoxyglycerin, PEG-12, PEG 135, PEG-150, PEG-20, PEG-8, pentylene glycol, hexylene glycol, phytantriol, poly quaternium-39 PPG-20 methyl glucose ether, propylene glycol, sodium hyaluronate, sodium lactate, sodium PCA, sorbitol, succinoglycan, synthetic beeswax, tri-C14-15 alkyl citrate, starch.

Suitable thickeners include e.g. acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, hydrogenated butylenes/ethylene/styrene copolymer.

Suitable humectants include e.g. adipic acid, fumaric acid and its salts, benzoic acid and its salts, glycerine triacetate, sodium or magnesium lauryl sulfate, magnesium stearate, solid polyethylenglycol, polyvinylpyrrolidone, boric acid, mono-laurate or mono-palmitate, myristyl alcohol, cetyl alcohol, cetylstearyl alcohol, talcum, calcium or magnesium salts of higher fatty acids, mono-, di- or triglycerides of higher fatty acids, polytetrafluorethylene.

Suitable antioxidants include e.g. sulfites, e.g. sodium sulfite, tocopherol or derivates thereof, ascorbic acid or derivates thereof, citric acid, propyl gallate, chitosan glycolate, cysteine, N-acetyl cysteine plus zinc sulfate, thiosulfates, e.g. sodium thiosulfate, polyphenols and the like.

The formulations and composition disclosed herein may further contain active ingredients, e.g. antimicrobials, anti-inflammatories, plant extracts, bisabolol, panthenol, tocopherol, actives for anti-stinging, anti-irritant or anti-dandruff applications, or anti-aging agents such as retinol, melibiose and the like. Other suitable actives include e.g. *Medicago officinalis, Actinidia chinensis*, allantoin, *Aloe barbadensis, Anona cherimolia, Anthemis nobilis, Arachis hypogaea, Arnica Montana, Avena sativa*, beta-carotene, bisabolol, *Borago officinalis*, butylenes glycol, *Calendula officinalis, Camellia sinensis*, camphor, *Candida bombicola*, capryloyl glycine, *Carica papaya, Centaurea cyanus*, cetylpyridinium chloride, *Chamomilla recutita, Chenopodium quinoa, Chinchona succirubra, Chondrus crispus, Citrus aurantium dulcis, Citrus grandis, Citrus limonum, Cocos nucifera, Coffea Arabica, Crataegus* monogina, *Cucumis melo*, dichlorophenyl imidazoldioxolan, *Enteromorpha compressa, Equisetum arvense*, ethoxydiglycol, ethyl panthenol, farnesol, ferulic acid, *Fragaria chiloensis, Gentiana lutea, Ginkgo biloba*, glycerin, glyceryl laurate, *Glycyrrhiza glabra, Hamamelis virginiana*, heliotropine, hydrogenated palm glycerides, citrates, hydrolyzed castor oil, hydrolyzed wheat protein, *Hypericum perforatum, Iris florentina, Juniperus communis, Lactis proteinum*, lactose, *Lawsonia inermis*, linalool, *Linum usitatissimum*, lysine, magnesium aspartate, *Magnifera indica, Malva sylvestris*, mannitol, *Melaleuca alternifolia, Mentha piperita*, menthol, menthyl lactate, *Mimosa tenuiflora, Nymphaea alba*, olaflur, *Oryza sativa*, panthenol, paraffinum liquidum, PEG-20M, PEG-26 jojoba acid, PEG-26 jojoba alcohol, PEG-35 castor oil, PEG-40 hydrogenated castor oil, PEG-60 hydrogenated castor oil, PEG-8 caprylic/capric acid, *Persea gratissima*, petrolatum, potassium aspartate, potassium sorbate, propylene glycol, *Prunus amygdalus dulcis, Prunus armeniaca, Prunus persica*, retinyl palmitate, *Ricinus communis, Rosa canina, Rosmarinus officinalis, Rubus idaeus*, salicylic acid, *Sambucus nigra*, sarcosine, *Serenoa serrulata, Simmondsia chinensis*, sodium carboxymethyl betaglucan, sodium cocoyl amino acids, sodium hyaluronate, sodium palmitoyl praline, stearoxytrimethylsilane, stearyl alcohol, sulfurized TEA-ricinoleate, talc, *Thymus vulgaris, Tilia cordata*, tocopherol, tocopheryl acetate, trideceth-9, *Triticum vulgare*, tyrosine, undecylenoyl glycine, urea, *Vaccinium myrtillus*, valine, zinc oxide, zinc sulfate.

The preservative composition of the present invention can be used in emulsions (both oil-in-water and water-in-oil), in aqueous solutions, in PIT (phase inversion temperature) emulsions, in oily solutions, in foaming cosmetic formulations (foams), and in so-called multiple emulsions, e.g. in triple emulsions (such as water/oil/water emulsions).

The preservative composition of the present invention can also be formulated as creams, gels, liquids or lotions. They can be used in hair care products such as shampoos, hair conditioners, hair dyes, hair tonic, hair gel, hair dressings, hair grooming aids and other hair care preparations; shaving applications such as shaving cream, aftershave lotions, and other shaving applications; personal cleaners for the body and hands, such as liquid bath soaps and detergents; fragrance preparations, such as perfumes, after bath splashes, and other similar fragrant preparations, skin care products, such as moisturizers, creams, and lotions and other similar skin care products, make-up products, such as mascara, base foundations and the like; make-up removal products, sun care products, indoor tanning products and other similar personal care products. In certain embodiments, the preservative composition disclosed herein may be incorporated in formulations used to saturate wipes, used for personal cleaning and hygiene (for example baby wipes, wet toilet wipes, make-up removal wipes and exfoliating wipes the like. The preservative composition may also be used in other formulations where preservative agents are needed.

In some embodiments, the preservative composition of the present invention may be added to an end-use formulation in an amount between 0.01% to about 10% by weight of the formulation. More particularly, in some embodiments the preservative composition is added in an amount which is between about 0.1% and 5.0% by weight of the formulation. The amount of the preservative composition added may be dependent on the preservative agent selected.

In certain embodiments, the preservative composition may be incorporated into home care products, such as hand-dish soaps, laundry detergents, cleaning wipes, all-purpose cleaners and other similar formulations that are used around the home.

In certain embodiments, the preservative composition may be included in wet wipe formulations that are used to saturate a wet wipe. In these embodiments, the preservative composition may serve to preserve the wet wipe formulation and the wet wipe prior to use. Once the wet wipe composition is formulated, the wet wipe composition is applied to a substrate.

The wet wipe composition with the preservative composition contained therein, may be applied to a substrate to be treated using conventional application techniques. Conventional techniques can include spraying, pouring, squirting and/or wiping the formulation on a substrate. In some embodiments, the wet wipe composition is provided to the end user as a ready-to-use formulation or is provided to the end user in a container with an application means. For example, the wet wipe composition may be provided in a container which is pressurized as an aerosol, a container with a trigger or pump sprayer, as a squirt container or conventional containers with a removable cap that allows the user to pour the formulation onto a substrate.

However, in certain embodiments, the wet wipe formulation containing the preservative composition disclosed herein may be impregnated or applied to a wipe substrate. In this embodiment, the wipe is a single use wipe that is impregnated with the formulation and is stored in a container that will dispense the wipe to a user. The container with the wipes may contain a single wipe, or several wipes. Suitable containers include a pouch containing a single wipe, such as a moist towelette which is torn open by the user or may be a pouch with a resealable opening containing several wipes in a stacked fashion or other suitable formation that would allow a single wipe to be removed from the opening at a time. Pouches are generally prepared form a fluid impervious material, such as a film, a coated paper or foil or other similar fluid impervious materials. In certain embodiments, the wipe may be placed into a fluid impervious container having an opening to access the wipes in the container. In this manner, the user may remove one or more wipes from the opening in the container. Suitable containers can include molded plastic containers having lids that are generally fluid impervious. The lid may have an opening to access the wipes in the container. The wipes in the container may be situated in the container in an interleaved stacked, such that as a wipe is removed from the container the next wipe is positioned in the opening of the container ready for the user to remove the next wipe. Alternatively, in certain embodiments, the wipe may be a continuous material which is perforated between the individual wipes of the continuous material. The continuous wipe material with perforations may be in a folded form or may be in a rolled form. Generally, in the rolled form, the wipe material is fed from the center of the rolled material and through the opening of the lid of the container for dispensing. As with the interleaved stack, as a wipe is removed from the container, the next wipe is positioned in the opening for the user to remove the next wipe, when needed.

Disposable wipes provide advantages over other application vehicles, such as a reusable sponge, rag or the like. Particularly advantageous is the fact that the impregnated wipe is used a single time and then disposed of, which is contrary to the use of sponges, rags and the like, which may be used repeatedly.

In some embodiments, the formulation containing the preservative composition disclosed herein is impregnated into a wipe such that the wipe is pre-moistened and will express or release the formulation on to the substrate as the wipe is applied to the substrate to be treated. Generally, the formulation is saturated into the wipe such that the wipe will release the formulation to the substrate through wiping action.

Suitable wipe substrates include woven and nonwoven materials. In certain embodiments, any nonwoven web material may be used. Exemplary nonwoven materials may include, but are not limited to meltblown, coform, spunbond, airlaid, airlaced, hydroentangled nonwovens, spunlace, bonded carded webs, and laminates thereof. The fibers used to prepare the wipe substrate may be cellulosic fiber, thermoplastic fibers and mixtures thereof. The fibers may also be continuous fibers, discontinuous fibers, staple fibers and mixtures thereof. Basis weights of the nonwoven web may vary from about 12 grams per square meter to 200 grams per square meter (gsm) or more.

In one embodiment, the substrate impregnated with the wiping composition contains significant amounts of cellulosic fibers. In particular, the wiping composition of the present invention is particularly well suited for protecting the cellulose substrate from attack by microorganisms that can contaminate the product. In one particular embodiment, for instance, the substrate may be made from greater than 80%, such as greater than 85%, such as greater than 90%, such as greater than 95%, such as even 100% by weight cellulose fibers. For examples, in one embodiment, the substrate is made from pulp fibers and a binder in an airlaced process. The basis weight of the substrate can be from about 20 gsm to about 100 gsm, such as from about 40 gsm to about 70 gsm, such as from about 50 gsm to about 60 gsm.

Once incorporated into the substrate, the resulting wiping product can have a weight ratio of liquid to substrate of from about 5:1 to about 1:1, such as from about 2:1 to about 4:1.

The following examples illustrate the invention without limitation. All parts and percentages provided are by weight unless otherwise indicated.

It will be understood that each of the elements described in the examples below, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims.

EXAMPLES

To demonstrate the synergistic effect, the following examples were performed. In the examples below, the propylene glycol caprylate (PGC) used is a mixture of propylene glycol monocaprylates (octanoic acid-2-hydroxy-1-methylethyl ester and 2-hydroxylpropyl caprylate) and propylene glycol dicaprylate (1,2-propylene glycol dicaprylate), the mixture comprising about 74 wt.-% of the propylene glycol monocaprylates and about 26 wt.-% of the propylene glycol dicaprylate.

Example 1

The synergistic preservative effect of propylene glycol caprylate (PGC) with Phenoxyethanol in non-ionic lotion matrices was tested.

Method

Test Organism Preparation

The challenge microorganisms used in this study are: *Pseudomonas aeruginosa* ATCC 9027/DSM 1128, *Pluralibacter gergoviae* ATCC 33028/DSM 9245, *Staphylococcus aureus* ATCC 6538/DSM 799, *Burkholderia cepacia* ATCC 25416/DSM 7288, *Klebsiella pneumoniae* ATCC 10031/DSM 681, *Escherichia coli* ATCC 8739/DSM 1576, *Candida albicans* ATCC 10231/DSM 1386 and *Aspergillus brasiliensis* ATCC 16404/DSM 1988.

Bacterial and yeast strains were kept cryofrozen; before use, they were sub-cultured onto tryptone soya agar (Bacteria) and malt extract agar (yeast), and incubated at the appropriate temperature and time. Each the bacteria and yeast test strains were harvested and suspended in diluent (saline tryptone water) to obtain a final concentration of bacteria of 1.0-5.0×$10^8$ cfu/ml and for yeast 1.0-5.0×$10^7$ cfu/ml. This was achieved using a calibration curve spectrophotometer at a wavelength of 620 nm.

*Aspergillus brasliensis* (mould) was kept cryofrozen at −80° C.; before use, they were sub-cultured onto MEA and incubated at 27.5±2.5° C. for 7-9 days (until spores are matured). Prior to testing, spores were harvested with sterile 0.05% polysorbate 80 solution and this suspension treated to remove fungal hyphae to obtain a final concentration of 1.0-5.0×$10^7$ cfu/ml.

The incubation conditions used for microorganism growth are summarized in Table 1.

TABLE 1

| Micro-organisms | Agar | Temp (° C.) | Time |
|---|---|---|---|
| *Pseudomonas aeruginosa* ATCC 9027 | TSA | 30 ± 2 | 24 ± 2 hours |
| *Pluralibacter gergoviae* ATCC 33028 | TSA | 30 ± 2 | 24 ± 2 hours |
| *Staphylococcus aureus* ATCC 6538 | TSA | 30 ± 2 | 24 ± 2 hours |
| *Burkholderia cepacia* ATCC 25416 | TSA | 30 ± 2 | 24 ± 2 hours |
| *Klebsiella pneumonia* ATCC 10031 | TSA | 30 ± 2 | 24 ± 2 hours |
| *Escherichia coli* ATCC 8739 | MEA | 30 ± 2 | 24 ± 2 hours |
| *Candida albicans* ATCC 10231 | MEA | 27.5 ± 2.5 | 48 ± 2 hours |
| *Aspergillus brasiliensis* ATCC 16404 | MEA | 27.5 ± 2.5 | 7-9 days |

To establish the precise CFU/ml of the inoculum culture a 1 ml aliquot was then taken from each bacterial, yeast and mould suspension and serially diluted down to $10^{-1}$ for bacteria and $10^{-6}$ for yeast and mould, 1 ml of each dilution was then plated in duplicate using the pour plate method and incubated at the appropriate temperature and time.

The incubation conditions used for microorganism growth are summarized in Table 2.

TABLE 2

| Micro-organisms | Agar | Temp (° C.) | Time |
|---|---|---|---|
| Bacteria | TSA | 30 ± 2 | Up to 2 days |
| Yeast | MEA | 27.5 ± 2.5 | Up to 3 days |
| Mould | MEA | 27.5 ± 2.5 | Up to 3 days |

Test Sample Preparation

For each organism tested, 19.8 g of each preservative composition sample was prepared in a non-ionic lotion formulation. The samples used in this study are summarized in Table 3 below.

Samples 6, 7, 12 and 13 were not tested against *A. brasiliensis*.

TABLE 3

| Sample number | Phenoxyethanol Concentration (ppm) | Propyleneglycol capylate Concentration (ppm) | Matrices | Sample weight |
|---|---|---|---|---|
| 1 | 0 | 0 | Non-ionic lotion | 19.8 g |
| 2 | 5000 | 0 | Non-ionic lotion | 19.8 g |
| 3 | 6000 | 0 | Non-ionic lotion | 19.8 g |
| 4 | 7000 | 0 | Non-ionic lotion | 19.8 g |
| 5 | 8000 | 0 | Non-ionic lotion | 19.8 g |
| 6 | 9000 | 0 | Non-ionic lotion | 19.8 g |
| 7 | 10000 | 0 | Non-ionic lotion | 19.8 g |
| 8 | 3000 | 2000 | Non-ionic lotion | 19.8 g |

TABLE 3-continued

| Sample number | Phenoxyethanol Concentration (ppm) | Propyleneglycol capylate Concentration (ppm) | Matrices | Sample weight |
|---|---|---|---|---|
| 9 | 3600 | 2400 | Non-ionic lotion | 19.8 g |
| 10 | 4200 | 2800 | Non-ionic lotion | 19.8 g |
| 11 | 5000 | 3000 | Non-ionic lotion | 19.8 g |
| 12 | 5600 | 3400 | Non-ionic lotion | 19.8 g |
| 13 | 6000 | 4000 | Non-ionic lotion | 19.8 g |

Non-Ionic Lotion Formulation

The composition of the non-ionic lotion formulation is provided in the following.

| Ingredient | Tradename | Active in formulation % by wt. | Active in raw material % by wt. | Raw material in formulation % by wt. |
|---|---|---|---|---|
| Cetearyl alcohol | — | 2 | 100 | 2 |
| Light mineral oil | — | 5 | 100 | 5 |
| Glyceryl stearate and PEG100 stearate | Lonzest MSA | 2 | 100 | 2 |
| Glycerine | — | 2.5 | 100 | 2.5 |
| Xanthan Gum | — | 0.2 | 100 | 0.2 |
| NaOH/Citric acid | — | | Adjust to pH 6 | |
| DI Water | — | To 100% | 100 | To 100% |

Test Procedure

Samples were inoculated on Day 0. Preservation efficacy testing starts upon sample inoculation. Preservation efficacy testing was performed over a period of 28 days.

Test samples were inoculated with separate inoculums. Inoculums did not exceed <1% of the total sample volume.

The total microbial load in sample for a bacterial suspension test was $1\times10^{6}$-$1\times10^{7}$ cfu/ml and the total load for a fungal suspension test should be $1\times10^{5}$-$1\times10^{6}$ cfu/ml.

Each inoculated sample was mixed until a homogenous mixture was obtained.

Samples are tested at Day(s) 0, 7, 14, 21 and 28 after inoculation. Additional testing was also performed for samples 2, 3, 4, 8, 9 and 10 on day 2.

Upon reaching the specified contact time a 1 ml aliquot of each test sample was added to 9 ml of neutralizing broth and the whole solution was mixed.

Subsequent dilutions were prepared by serial dilution to $10^{-5}$.

For each dilution prepare duplicate 1 ml pour plates using appropriate agar and incubate at the appropriate temperature and time as in Table 2.

Pour plates were prepared for each sample dilution aliquot by pouring 20-25 ml of agar into the plate, mixing thoroughly and allowing the agar to set.

Limits of Detection

Depending on the dilution parameters of a method and the techniques used to recover cells, specific limits of detection must be set to ensure reliable enumeration.

Wherever possible the dilution giving between 10 and 330 colonies per plate was counted and the average of the duplicate plates was used to calculate the number of colony forming units per ml of the sample. If no growth is found on any plate, the results are reported as "<10" CFU/ml at $10^{-1}$.

For example, if a plate had 7 visible colonies countable, <10 would be recorded and 10 would be used for the calculation. For the upper limit, if 407 colonies were counted on a plate, >330 would be recorded and 330 would be used for the calculation.

Calculation of Recovery.

The recovery count per ml of sample is calculated as follows:

Enumeration and Calculation of N (Inoculum Culture)

Because there is a 1 in 100 dilution of the inoculum culture when added to the product during the test, the count per ml of sample is calculated as follows:

Organisms per ml inoculum culture/100=organisms CFU per ml sample.

Enumeration and Calculation of T (Test Sample)

The mean average of CFU per 1 ml aliquot from duplicate plates was established using the below calculation;

Organisms per ml test sample/2=organism recovery per ml sample.

Both N (inoculum culture) and T (Test sample) underwent a number of dilutions. To account for this a final multiplication of the dilution factor is applied to both.

Log Reduction Calculations (N_T)

Before calculating the log reduction both N and T were converted into a logarithm base 10 value.

To calculate the final log reduction the following calculation was used:

$$\text{Log } N - \text{log } T = \text{log reduction}$$

Results

The inoculum concentrations used for each sample and each organism are detailed below.

*Pseudomonas aeruginosa* ATCC 9027—

| Sample number | Inoculum concentration CFU/ml |
|---|---|
| 1 | $5.00\times10^{6}$ |
| 2 | $6.30\times10^{6}$ |
| 3 | $6.30\times10^{6}$ |
| 4 | $6.30\times10^{6}$ |
| 5 | $5.00\times10^{6}$ |
| 6 | $5.00\times10^{6}$ |
| 7 | $5.00\times10^{6}$ |
| 8 | $6.30\times10^{6}$ |
| 9 | $6.30\times10^{6}$ |
| 10 | $6.30\times10^{6}$ |
| 11 | $5.00\times10^{6}$ |
| 12 | $5.00\times10^{6}$ |
| 13 | $5.00\times10^{6}$ |

*Pluralibacter gergoviae* ATCC 33028

| Sample number | Inoculum concentration CFU/ml |
|---|---|
| 1 | 4.75 × $10^6$ |
| 2 | 3.50 × $10^6$ |
| 3 | 3.50 × $10^6$ |
| 4 | 3.50 × $10^6$ |
| 5 | 4.75 × $10^6$ |
| 6 | 4.75 × $10^6$ |
| 7 | 4.75 × $10^6$ |
| 8 | 3.50 × $10^6$ |
| 9 | 3.50 × $10^6$ |
| 10 | 3.50 × $10^6$ |
| 11 | 4.75 × $10^6$ |
| 12 | 4.75 × $10^6$ |
| 13 | 4.75 × $10^6$ |

*Staphylococcus aureus* ATCC 6538

| Sample number | Inoculum concentration CFU/ml |
|---|---|
| 1 | 4.35 × $10^6$ |
| 2 | 4.35 × $10^6$ |
| 3 | 4.35 × $10^6$ |
| 4 | 4.35 × $10^6$ |
| 5 | 4.35 × $10^6$ |
| 6 | 4.35 × $10^6$ |
| 7 | 4.35 × $10^6$ |
| 8 | 4.35 × $10^6$ |
| 9 | 4.35 × $10^6$ |
| 10 | 4.35 × $10^6$ |
| 11 | 4.35 × $10^6$ |
| 12 | 4.35 × $10^6$ |
| 13 | 4.35 × $10^6$ |

*Burkholderia cepacia* ATCC 25416

| Sample number | Inoculum concentration CFU/ml |
|---|---|
| 1 | 2.00 × $10^6$ |
| 2 | 2.65 × $10^6$ |
| 3 | 2.65 × $10^6$ |
| 4 | 2.65 × $10^6$ |
| 5 | 2.00 × $10^6$ |
| 6 | 2.00 × $10^6$ |
| 7 | 2.00 × $10^6$ |
| 8 | 2.65 × $10^6$ |
| 9 | 2.65 × $10^6$ |
| 10 | 2.65 × $10^6$ |
| 11 | 2.00 × $10^6$ |
| 12 | 2.00 × $10^6$ |
| 13 | 2.00 × $10^6$ |

*Klebsiella pneumonia* ATCC 10031

| Sample number | Inoculum concentration CFU/ml |
|---|---|
| 1 | 5.20 × $10^6$ |
| 2 | 3.40 × $10^6$ |
| 3 | 3.40 × $10^6$ |
| 4 | 3.40 × $10^6$ |
| 5 | 5.20 × $10^6$ |
| 6 | 5.20 × $10^6$ |
| 7 | 5.20 × $10^6$ |
| 8 | 3.40 × $10^6$ |
| 9 | 3.40 × $10^6$ |
| 10 | 3.40 × $10^6$ |
| 11 | 5.20 × $10^6$ |

-continued

| Sample number | Inoculum concentration CFU/ml |
|---|---|
| 12 | 5.20 × $10^6$ |
| 13 | 5.20 × $10^6$ |

*Escherichia coli* ATCC 8739

| Sample number | Inoculum concentration CFU/ml |
|---|---|
| 1 | 6.10 × $10^6$ |
| 2 | 6.10 × $10^6$ |
| 3 | 6.10 × $10^6$ |
| 4 | 6.10 × $10^6$ |
| 5 | 6.10 × $10^6$ |
| 6 | 6.10 × $10^6$ |
| 7 | 6.10 × $10^6$ |
| 8 | 6.10 × $10^6$ |
| 9 | 6.10 × $10^6$ |
| 10 | 6.10 × $10^6$ |
| 11 | 6.10 × $10^6$ |
| 12 | 6.10 × $10^6$ |
| 13 | 6.10 × $10^6$ |

*Candida albicans* ATCC 10231

| Sample number | Inoculum concentration CFU/ml |
|---|---|
| 1 | 5.65 × $10^5$ |
| 2 | 5.65 × $10^5$ |
| 3 | 5.65 × $10^5$ |
| 4 | 5.65 × $10^5$ |
| 5 | 5.65 × $10^5$ |
| 6 | 5.65 × $10^5$ |
| 7 | 5.65 × $10^5$ |
| 8 | 5.65 × $10^5$ |
| 9 | 5.65 × $10^5$ |
| 10 | 5.65 × $10^5$ |
| 11 | 5.65 × $10^5$ |
| 12 | 5.65 × $10^5$ |
| 13 | 5.65 × $10^5$ |

*Aspergillus brasiliensis* ATCC 16404

| Sample number | Inoculum concentration CFU/ml |
|---|---|
| 1 | 1.3 × $10^5$ |
| 2 | 1.3 × $10^5$ |
| 3 | 1.3 × $10^5$ |
| 4 | 1.3 × $10^5$ |
| 5 | 1.3 × $10^5$ |
| 8 | 1.3 × $10^5$ |
| 9 | 1.3 × $10^5$ |
| 10 | 1.3 × $10^5$ |
| 11 | 1.3 × $10^5$ |

In the following, the log reductions against each microorganism of sample formulations 1 to 13 according to Table 3 are provided.

| Organisms(s) | Sample | Log reduction Day 2 | Day 7 | Day 14 | Day 21 | Day 28 |
|---|---|---|---|---|---|---|
| *Pseudomonas aeruginosa* (ATCC 9027) | 1 | — | 0.18 | 0.31 | <0.00 | 0.02 |
| | 2 | >4.80 | >4.80 | >4.80 | >4.80 | >4.80 |
| | 3 | >4.80 | >4.80 | >4.80 | >4.80 | >4.80 |
| | 4 | >4.80 | >4.80 | >4.80 | >4.80 | >4.80 |
| | 5 | — | >4.70 | >4.70 | >4.70 | >4.70 |
| | 6 | — | >4.70 | >4.70 | >4.70 | >4.70 |
| | 7 | — | >4.70 | >4.70 | >4.70 | >4.70 |
| | 8 | >4.80 | >4.80 | >4.80 | >4.80 | >4.80 |
| | 9 | >4.80 | >4.80 | >4.80 | >4.80 | >4.80 |
| | 10 | >4.80 | >4.80 | >4.80 | >4.80 | >4.80 |
| | 11 | — | >4.70 | >4.70 | >4.70 | >4.70 |
| | 12 | — | >4.70 | >4.70 | >4.70 | >4.70 |
| | 13 | — | >4.70 | >4.70 | >4.70 | >4.70 |

| Organisms(s) | Sample | Log reduction Day 2 | Day 7 | Day 14 | Day 21 | Day 28 |
|---|---|---|---|---|---|---|
| *Pluralibacter gergoviae* (ATCC 33028) | 1 | — | 0.16 | 0.93 | 0.16 | 0.31 |
| | 2 | 2.93 | 3.90 | >4.54 | >4.54 | >4.54 |
| | 3 | >4.54 | >4.54 | >4.54 | >4.54 | >4.54 |
| | 4 | >4.54 | >4.54 | >4.54 | >4.54 | >4.54 |
| | 5 | — | >4.68 | >4.68 | >4.68 | >4.68 |
| | 6 | — | >4.68 | >4.68 | >4.68 | >4.68 |
| | 7 | — | >4.68 | >4.68 | >4.68 | >4.68 |
| | 8 | 2.54 | 3.89 | >4.54 | >4.54 | >4.54 |
| | 9 | >4.54 | >4.54 | >4.54 | >4.54 | >4.54 |
| | 10 | >4.54 | >4.54 | >4.54 | >4.54 | >4.54 |
| | 11 | — | >4.68 | >4.68 | >4.68 | >4.68 |
| | 12 | — | >4.68 | >4.68 | >4.68 | >4.68 |
| | 13 | — | >4.68 | >4.68 | >4.68 | >4.68 |

| Organisms(s) | Sample | Log reduction Day 2 | Day 7 | Day 14 | Day 21 | Day 28 |
|---|---|---|---|---|---|---|
| *Staphylococcus aureus* (ATCC 6538) | 1 | — | 0.42 | 1.26 | 2.42 | 1.67 |
| | 2 | 0.57 | 1.08 | 3.56 | >4.64 | >4.64 |
| | 3 | 1.06 | 2.98 | 4.24 | >4.64 | >4.64 |
| | 4 | 1.93 | 3.15 | 4.29 | >4.64 | >4.64 |
| | 5 | — | 3.05 | >4.64 | >4.64 | >4.64 |
| | 6 | — | 4.49 | >4.64 | >4.64 | >4.64 |
| | 7 | — | >4.64 | >4.64 | >4.64 | >4.64 |
| | 8 | 3.55 | >4.64 | >4.64 | >4.64 | >4.64 |
| | 9 | >4.64 | >4.64 | >4.64 | >4.64 | >4.64 |
| | 10 | >4.64 | >4.64 | >4.64 | >4.64 | >4.64 |
| | 11 | — | >4.64 | >4.64 | >4.64 | >4.64 |
| | 12 | — | >4.64 | >4.64 | >4.64 | >4.64 |
| | 13 | — | >4.64 | >4.64 | >4.64 | >4.64 |

| Organisms(s) | Sample | Log reduction Day 2 | Day 7 | Day 14 | Day 21 | Day 28 |
|---|---|---|---|---|---|---|
| *Burkholderia cepacia* (ATCC 25416) | 1 | — | <0.00 | <0.00 | <0.00 | <0.00 |
| | 2 | 2.71 | >4.42 | >4.42 | >4.42 | >4.42 |
| | 3 | 3.71 | >4.42 | >4.42 | >4.42 | >4.42 |
| | 4 | >4.42 | >4.42 | >4.42 | >4.42 | >4.42 |
| | 5 | — | >4.30 | >4.30 | >4.30 | >4.30 |
| | 6 | — | >4.30 | >4.30 | >4.30 | >4.30 |
| | 7 | — | >4.30 | >4.30 | >4.30 | >4.30 |
| | 8 | 3.19 | >4.42 | >4.42 | >4.42 | >4.42 |
| | 9 | >4.42 | >4.42 | >4.42 | >4.42 | >4.42 |
| | 10 | >4.42 | >4.42 | >4.42 | >4.42 | >4.42 |
| | 11 | — | >4.30 | >4.30 | >4.30 | >4.30 |

-continued

| Organisms(s) | Sample | Log reduction Day 2 | Day 7 | Day 14 | Day 21 | Day 28 |
|---|---|---|---|---|---|---|
| | 12 | — | >4.30 | >4.30 | >4.30 | >4.30 |
| | 13 | — | >4.30 | >4.30 | >4.30 | >4.30 |

| Organisms(s) | Sample | Log reduction Day 2 | Day 7 | Day 14 | Day 21 | Day 28 |
|---|---|---|---|---|---|---|
| *Klebsiella pneumoniae* (ATCC 10031) | 1 | — | <0.00 | 1.03 | 2.15 | 3.17 |
| | 2 | 0.22 | 1.34 | 3.78 | >4.53 | >4.53 |
| | 3 | 0.79 | 3.39 | >4.53 | >4.53 | >4.53 |
| | 4 | >4.53 | >4.53 | >4.53 | >4.53 | >4.53 |
| | 5 | — | >4.72 | >4.72 | >4.72 | >4.72 |
| | 6 | — | >4.72 | >4.72 | >4.72 | >4.72 |
| | 7 | — | >4.72 | >4.72 | >4.72 | >4.72 |
| | 8 | >4.53 | >4.53 | >4.53 | >4.53 | >4.53 |
| | 9 | >4.53 | >4.53 | >4.53 | >4.53 | >4.53 |
| | 10 | >4.53 | >4.53 | >4.53 | >4.53 | >4.53 |
| | 11 | — | >4.72 | >4.72 | >4.72 | >4.72 |
| | 12 | — | >4.72 | >4.72 | >4.72 | >4.72 |
| | 13 | — | >4.72 | >4.72 | >4.72 | >4.72 |
| *Eschericia coli* (ATCC 8739) | 1 | — | 1.69 | 3.74 | 4.28 | 4.61 |
| | 2 | 0.38 | 1.32 | 3.85 | >4.79 | >4.79 |
| | 3 | 2.69 | 3.48 | >4.79 | >4.79 | >4.79 |
| | 4 | 3.57 | >4.79 | >4.79 | >4.79 | >4.79 |
| | 5 | — | >4.79 | >4.79 | >4.79 | >4.79 |
| | 6 | — | >4.79 | >4.79 | >4.79 | >4.79 |
| | 7 | — | >4.79 | >4.79 | >4.79 | >4.79 |
| | 8 | 3.22 | >4.79 | >4.79 | >4.79 | >4.79 |
| | 9 | >4.79 | >4.79 | >4.79 | >4.79 | >4.79 |
| | 10 | >4.79 | >4.79 | >4.79 | >4.79 | >4.79 |
| | 11 | — | >4.79 | >4.79 | >4.79 | >4.79 |
| | 12 | — | >4.79 | >4.79 | >4.79 | >4.79 |
| | 13 | — | >4.79 | >4.79 | >4.79 | >4.79 |

| Organisms(s) | Sample | Log reduction Day 2 | Day 7 | Day 14 | Day 21 | Day 28 |
|---|---|---|---|---|---|---|
| *Candida albicans* (ATTC 10231) | 1 | — | 0.63 | 0.23 | 0.23 | 0.23 |
| | 2 | — | 0.85 | 0.62 | 0.99 | 1.71 |
| | 3 | — | 0.63 | 1.21 | >3.75 | >3.75 |
| | 4 | — | 0.60 | 3.33 | >3.75 | >3.75 |
| | 5 | — | 0.61 | >3.75 | >3.75 | >3.75 |
| | 6 | — | 1.25 | >3.75 | >3.75 | >3.75 |
| | 7 | — | 1.87 | >3.75 | >3.75 | >3.75 |
| | 8 | — | 2.99 | >3.75 | >3.75 | >3.75 |
| | 9 | — | >3.75 | >3.75 | >3.75 | >3.75 |
| | 10 | — | >3.75 | >3.75 | >3.75 | >3.75 |
| | 11 | — | >3.75 | >3.75 | >3.75 | >3.75 |
| | 12 | — | >3.75 | >3.75 | >3.75 | >3.75 |
| | 13 | — | >3.75 | >3.75 | >3.75 | >3.75 |

| Organisms(s) | Sample | Log reduction Day 2 | Day 7 | Day 14 | Day 21 | Day 28 |
|---|---|---|---|---|---|---|
| *Apsergillus brasiliensis* (ATCC 16404) | 1 | — | 0.51 | 0.21 | 0.41 | 0.41 |
| | 2 | — | 0.81 | 1.16 | 0.30 | 0.72 |
| | 3 | — | 088 | 1.51 | 2.27 | 3.41 |
| | 4 | — | 1.41 | 2.03 | 2.81 | 3.34 |
| | 5 | — | 1.64 | 2.21 | 3.16 | 3.81 |
| | 8 | — | 0.97 | 1.51 | 1.88 | 1.88 |
| | 9 | — | 1.70 | 2.11 | 2.16 | 2.51 |
| | 10 | — | 2.16 | 2.64 | 3.11 | 3.21 |
| | 11 | — | 3.51 | 3.81 | >4.11 | >4.11 |

The synergistic preservative effect of propylene glycol caprylate (PGC) with Phenoxyethanol is observed against *Staphylococcus aureus* ATCC 6538/DSM 799, *Burkholderia cepacia* ATCC 25416/DSM 7288, *Klebsiella pneumoniae* ATCC 10031/DSM 681, *Escherichia coli* ATCC 8739/DSM 1576, *Candida albicans* ATCC 10231/DSM 1386 and *Aspergillus brasiliensis* ATCC 16404/DSM 1988.

Propylene glycol caprylate (PGC) with Phenoxyethanol was also effective against *Pseudomonas aeruginosa* ATCC 9027/DSM 1128 and *Pluralibacter gergoviae* ATCC 33028/DSM 9245.

Example 2

The synergistic preservative effect of propylene glycol caprylate (PGC) with Phenoxyethanol in a Hair Conditioner matrices was tested.

Method

Test Organism Preparation

The challenge microorganisms used in this study are: *Candida albicans* ATCC 10231/DSM 1386 and *Aspergillus brasiliensis* ATCC 16404/DSM 1988.

The test organisms were prepared according to the protocol of Example 1.

Test Sample Preparation

For each organism tested, 19.8 g of each preservative composition sample was prepared in a hair conditioner formulation. The samples used in this study are summarized in Table 4.

TABLE 4

| Sample number | Phenoxyethanol Concentration (ppm) | Propyleneglycol capylate Concentration (ppm) | Matrices | Sample weight |
|---|---|---|---|---|
| 1 | 0 | 0 | Hair Conditioner | 19.8 g |
| 2 | 3000 | 0 | Hair Conditioner | 19.8 g |
| 3 | 4000 | 0 | Hair Conditioner | 19.8 g |
| 4 | 5000 | 0 | Hair Conditioner | 19.8 g |
| 5 | 1800 | 1200 | Hair Conditioner | 19.8 g |
| 6 | 2400 | 1600 | Hair Conditioner | 19.8 g |
| 7 | 3000 | 2000 | Hair Conditioner | 19.8 g |

Hair Conditioner Formulation

The composition of the hair conditioner formulation is provided in the following.

| Ingredient | Tradename | Active in formulation % by wt. | Active in raw material % by wt. | Raw material in formulation % by wt. |
|---|---|---|---|---|
| Stearamidopropyl dimethylamine | Lexamine S13 | 1.35 | 100 | 1.35 |
| Cetearyl alcohol | — | 3 | 100 | 3 |
| KCL | — | 0.15 | 100 | 0.15 |
| Lactic acid | Purac HS88 | 0.37 | 88 | 0.42 |
| DI Water | — | To 100% | 100 | To 100% |

Test Procedure

Samples were inoculated on Day 0. Preservation efficacy testing starts upon sample inoculation.

Test samples were inoculated with separate inoculums. Inoculums did not exceed <1% of the total sample volume.

The total microbial load in sample for a fungal suspension test should be $1\times10^5$-$1\times10^6$ cfu/ml.

Each inoculated sample was mixed until a homogenous mixture was obtained.

Samples are tested at Day(s) 0, 2, 7, 14, and 28 after inoculation.

Upon reaching the specified contact time a 1 ml aliquot of each test sample was added to 9 ml of neutralizing broth and the whole solution was mixed.

Subsequent dilutions were prepared by serial dilution to $10^{-5}$.

For each dilution prepare duplicate 1 ml pour plates using appropriate agar and incubate at the appropriate temperature and time as in Table 2.

Pour plates were prepared for each sample dilution aliquot by pouring 20-25 ml of agar into the plate, mixing thoroughly and allowing the agar to set.

Limits of Detection

Limits of detection and calculation of recovery were determined as in Example 1.

Results

The inoculum concentrations used for each sample and each organism are detailed below.

*Candida albicans* ATCC 10231

| Sample number | Inoculum concentration CFU/ml |
|---|---|
| 1 | $1.55 \times 10^5$ |
| 2 | $1.55 \times 10^5$ |
| 3 | $1.55 \times 10^5$ |
| 4 | $1.55 \times 10^5$ |
| 5 | $1.55 \times 10^5$ |
| 6 | $1.55 \times 10^5$ |
| 7 | $1.55 \times 10^5$ |

*Aspergillus brasiliensis* ATCC 16404

| Sample number | Inoculum concentration CFU/ml |
|---|---|
| 1 | $1.05 \times 10^5$ |
| 2 | $1.05 \times 10^5$ |
| 3 | $1.05 \times 10^5$ |
| 4 | $1.05 \times 10^5$ |
| 5 | $1.05 \times 10^5$ |

-continued

| Sample number | Inoculum concentration CFU/ml |
|---|---|
| 6 | $1.05 \times 10^5$ |
| 7 | $1.05 \times 10^5$ |

In the following, the log reductions against each microorganism of sample formulations 1 to 7 according to Table 4 are provided.

| | | Log reduction | | | | |
|---|---|---|---|---|---|---|
| Organisms(s) | Sample | Day 2 | Day 7 | Day 14 | Day 21 | Day 28 |
| *Candida albicans* (ATTC 10231) | 1 | 0.61 | 0.87 | 0.94 | | 2.76 |
| | 2 | >3.19 | >3.19 | >3.19 | | >3.19 |
| | 3 | >3.19 | >3.19 | >3.19 | | >3.19 |
| | 4 | >3.19 | >3.19 | >3.19 | | >3.19 |
| | 5 | >3.19 | >3.19 | >3.19 | | >3.19 |
| | 6 | >3.19 | >3.19 | >3.19 | | >3.19 |
| | 7 | >3.19 | >3.19 | >3.19 | | >3.19 |

The hair conditioner unpreserved (sample 1) is unable to deliver effective preservation against *Candida albicans.*

Sample numbers 2, 3, and 4 delivered >3.19 log reduction (total kill) against *Candida albicans.*

Similarly samples 5, 6, and 7 delivered the same >3.19 log reduction (total kill) against *Candida albicans* however these samples contained a lower concentration of phenoxyethanol preservative.

| | | Log reduction | | | | |
|---|---|---|---|---|---|---|
| Organisms(s) | Sample | Day 2 | Day 7 | Day 14 | Day 21 | Day 28 |
| *Aspergillus brasiliensis* (ATCC 16404) | 1 | 0.42 | 0.43 | 0.46 | | 0.82 |
| | 2 | 0.61 | 0.68 | 0.88 | | 1.12 |
| | 3 | 0.68 | 0.98 | 1.36 | | 1.56 |
| | 4 | 0.77 | 1.24 | 1.56 | | 1.62 |
| | 5 | 1.45 | 1.94 | 2.32 | | 2.52 |
| | 6 | 1.62 | 2.32 | 2.42 | | 2.74 |
| | 7 | 1.77 | 2.42 | 2.74 | | 2.82 |

The hair conditioner sample numbers 4, 5 and 6 gave much greater levels of log reduction at the same time points when compared to sample numbers 2, 3 and 4 against *Aspergillus brasiliensis.*

Example 3

This example details the synergistic preservative effect of propylene glycol caprylate (PGC) with various preservative agents in a simple water matrices. The following example demonstrates the synergistic preservative effect of combining various different preservatives with an alkylene glycol ester.

The challenge microorganisms used in this study are: *Pluralibacter gergoviae* ATCC 33028/DSM 9245, *Candida albicans* ATCC 10231/DSM 1386 and *Aspergillus brasiliensis* ATCC 16404/NCPF 2275.

Method

Test Organism Preparation

Bacterial and yeast strains were kept cryofrozen at −80° C.; before use, they were sub-cultured onto tryptone soya agar (Bacteria) and malt extract agar (yeast), and incubated at the appropriate temperature and time.

The incubation conditions used for microorganism growth are summarized in Table 5.

TABLE 5

| Micro-organisms | Agar | Temp (° C.) | Time |
|---|---|---|---|
| *Pluralibacter gergoviae* ATCC 33028 | TSA | 30 ± 2 | 24 ± 2 hours |
| *Candida albicans* ATCC 10231 | MEA | 30 ± 2 | 48 ± 2 hours |

*Aspergillus brasiliensis* ATCC 16404/NCPF 2275 used in these experiments was prepared from a $1\times10^8$ BioBall M/S10E8 *A. brasiliensis* (Biomerieux) in 1 ml BioBall 14 Day Re-Hydration Fluid (Biomerieux). A test suspension was then created in tryptone buffered saline and adjusting the cell concentration to between $1\times10^5$ and $5\times10^6$ CFU/ml.

A test suspension was then created for each the bacteria and yeast by adding loopfuls of organism to sterile distilled water and adjusting the cell concentration to between $1\times10^8$ and $5\times10^9$ CFU/ml for bacteria, and $1\times10^6$ and $5\times10^7$ CFU/ml for yeast. This was achieved using the data from a calibration curve generated by a spectrophotometer at a wavelength of 620 nm.

The incubation conditions used for microorganism growth are summarized in Table 6.

TABLE 6

| Micro-organisms | Agar | Temp (° C.) | Time |
|---|---|---|---|
| Bacteria | TSA | 30 ± 2 | Up to 2 days |
| Yeast | MEA | 27.5 ± 2.5 | Up to 3 days |
| Mould | MEA | 27.5 ± 2.5 | Up to 3 days |

Test Sample Preparation

For each organism tested, 1 g of each preservative agent and PGC composition sample was prepared in sterile distilled water. The samples used in this study are summarized in Table 7 below.

TABLE 7

| Sample | | Concentrations (ppm) | | | PGC concentrations (ppm) | | | Contact time | | |
|---|---|---|---|---|---|---|---|---|---|---|
| (preservative agent) | Chemistry | P.g. | C.a. | A.b. | P.g. | C.a. | A.b. | P.g. | C.a. | A.b. |
| Bis (3-aminopropyl) dodecylamine | Triamine | 0, 5, 12.5, 25, 50, 100 | 0, 10, 20, 40, 60, 80 | Not available | 0, 5, 12.5, 25, 50, 100 | 0, 10, 25, 50, 100, 200 | Not available | 5 min | 5 min | N/A |
| Didecyl dimethyl ammonium chloride | QAC | Not available | 0, 10, 20, 30, 40, 50 | 0, 10, 20, 30, 40, 50 | Not available | 0, 10, 25, 50, 100, 200 | 0, 10, 25, 50, 100, 200 | N/A | 5 min | 5 min |
| Sodium Benzoate | Organic acid | 0, 2000, 5000, 10000, 20000, 30000 | 0, 10000, 20000, 30000, 40000, 50000 | 0, 10000, 20000, 30000, 40000, 50000 | 0, 5, 12.5, 25, 50, 100 | 0, 10, 25, 50, 100, 200 | 0, 10, 25, 50, 100, 200 | 48 hours | 48 hours | 72 hours |

TABLE 7-continued

| Sample | | Concentrations (ppm) | | | PGC concentrations (ppm) | | | Contact time | | |
|---|---|---|---|---|---|---|---|---|---|---|
| (preservative agent) | Chemistry | P.g. | C.a. | A.b. | P.g. | C.a. | A.b. | P.g. | C.a. | A.b. |
| Lactic Acid | Organic acid | 0, 200, 500, 1000, 1500, 2000 | Not available | 0, 100, 250, 500, 1000, 2500 | 0, 10, 25, 50, 100, 200 | Not available | 0, 10, 25, 50, 100, 200 | 3 hours | N/A | 3 hours |
| Benzyl Alcohol | Phenolic alcohol | 0, 500, 1000, 2000, 3000, 4000 | Not available | Not available | 0, 10, 25, 50, 100, 200 | Not available | Not available | 7 days | N/A | N/A |
| Phenoxyethanol | Phenolic alcohol | 0, 1000, 2500, 5000, 7500, 10000 | 0, 1000, 2500, 5000, 7500, 10000 | 0, 1000, 2500, 5000, 7500, 10000 | 0, 10, 25, 50, 100, 200 | 0, 10, 25, 50, 100, 200 | 0, 10, 25, 50, 100, 200 | 24 hours | 24 hours | 48 hours |
| Benzisothiazolinone | Isothiazolinone | 0, 12.5, 25, 50, 100, 200 | 0, 50, 100, 250, 500, 1000 | 0, 50, 100, 250, 500, 1000 | 0, 10, 25, 50, 100, 200 | 0, 10, 25, 50, 100, 200 | 0, 10, 25, 50, 100, 200 | 48 hours | 48 hours | 48 hours |
| Sorbic Acid | Organic Acid | 0, 100, 200, 300, 400, 500 | Not available | Not available | 0, 10, 25, 50, 100, 200 | Not available | Not available | 3 hours | N/A | N/A |
| Dehydroacetic acid | Organic Acid | Not available | 0, 1000, 2000, 3000, 4000, 5000 | Not available | Not available | 0, 10, 25, 50, 100, 200 | Not available | N/A | 14 days | N/A |

Test Procedure

Each test sample was prepared by inoculating 1 ml aliquot of the test organism suspension into 1 ml of test sample.

The combination was then mixed. Each test mixture was sampled and tested at a defined time point after inoculation. The contact times used in this study are detailed in Table 7 above.

Upon reaching the specified contact time the test mixture was deactivated by adding a 100 μl of test mixture into 900 μl of neutralizing broth and the whole solution was mixed. The solution was left for 5 minutes to ensure the action of the preservative agent was effectively neutralized. Subsequent dilutions were prepared by adding 100 μl into 900 μl of neutralizing broth.

For each dilution prepare drop plates using appropriate agar and incubate at the appropriate temperature and time as in Table 5.

Plating

Used the drop plate technique.

Prepare agar plates by drying for 45 min-1 hour in a laminar flow at 20-25° C. Aliquot 0.025 ml drops onto the agar surface for each sample dilution. Allow drops to dry and incubate appropriately.

Plates were plates were prepared in sextuplicate for each for each sample dilution.

Limits of Detection

Depending on the dilution parameters of a method and the techniques used to enumerate cells, specific limits of detection must be set to ensure reliable enumeration.

For counting of drop plates, colonies from the incubated plates were enumerated using the lower count limit of <0.25 CFU/0.025 ml and the upper count limit of >8.25 CFU/0.025 ml across all 6 drops. When dilution factors are taken into account this results in a lower limit of <10 CFU/ml and an upper limit of >330 CFU/ml.

The upper and lower limits for drop plating were only employed on the highest and lowest dilution factor plates.

For example if the lowest dilution plate e.g. $10^{-1}$ had a mean of 0 visible colonies, <0.25 would be recorded and 0.25 would be used for the calculation.

Similarly for the upper limit on the highest dilution plate e.g. $10^{-4}$, had a mean of 31 colonies counted and >8.25 would be recorded and 8.25 would be used for the calculation.

The lowest dilution factor plate used for all organisms was $10^1$. The highest dilution factor plate used for *Pluralibacter gergoviae* was $10^1$, for *Candida albicans* 104 and *Aspergillus brasiliensis* $10^{-3}$.

When reporting the final log reduction value, if a lower limit of detection has been used to make the calculation a ">" value will be reported for example ">5.02 log reduction", while if upper limit of detection has been used to make the calculation a "<" value will be reported for example "<2.92 log reduction".

Calculation of Recovery:

The recovery count per ml of sample is calculated as follows:

Enumeration and Calculation of N (Water Control)

The mean average of cfu per 0.025 ml drops was established using the below calculation;

$$N = \left(\frac{d_1}{6}\right)$$

Where $d_1$ is sum of viable count values from 6 drops

This was then multiplied by 40 to establish cfu/ml;

Enumeration and Calculation of T (Test Sample)

First, the mean average of cfu per 0.025 ml drops was established using the below calculation;

$$T = \left(\frac{d_1}{6}\right)$$

Where $d_1$ is sum of viable count values from 6 drops

This was then multiplied by 40 to establish cfu/ml;

Both N (water control) and T (Test sample) underwent a number of dilutions. To account for this a final multiplication of the dilution factor is applied to both.

Log Reduction Calculations (N_T)

Before calculating the log reduction both N and T were converted into a logarithm base 10 value.

To calculate the final log reduction the following calculation was used:

$$\text{Log } 10\ N - \log 10\ T = \log \text{ reduction}$$

Results

The propylene glycol caprylate (PGC) was tested in combination with Bis (3-aminopropyl) dodecylamine, didecyl dimethyl ammonium chloride, sodium benzoate, lactic acid, benzyl alcohol, phenoxyethanol, benzisothiazolinone, sorbic acid and dehydroacetic acid.

The concentration of the propylene glycol caprylate and the concentration of the preservative were varied. Log reductions are provided in the tables below.

The following results were obtained:

Concentrations of Bis (3-aminopropyl) dodecylamine and PGC were tested against *P. gergoviae*, and *C. albicans*. In the following, the log reductions against each microorganism is provided.

*P. gergoviae*—

| | | Bis (3-aminopropyl) dodecylamine Concentration | | | | | |
|---|---|---|---|---|---|---|---|
| | | 0 ppm | 5 ppm | 12.5 ppm | 25 ppm | 50 ppm | 100 ppm |
| PGC Concentration | 0 ppm | | 0.01 | 0.00 | 2.00 | >5.52 | >5.52 |
| | 5 ppm | 0.00 | 0.00 | 0.28 | 2.00 | >5.52 | >5.52 |
| | 12.5 ppm | 0.00 | 0.04 | 1.71 | 1.64 | >5.52 | >5.52 |
| | 25 ppm | 0.01 | 0.00 | 1.40 | >5.52 | >5.52 | >5.52 |
| | 50 ppm | 0.00 | 0.00 | 2.13 | >5.52 | >5.52 | >5.52 |
| | 100 ppm | 0.00 | 0.00 | 1.72 | >5.52 | >5.52 | >5.52 |

*C. albicans*—

| | | Bis (3-aminopropyl) dodecylamine Concentration | | | | | |
|---|---|---|---|---|---|---|---|
| | | 0 ppm | 10 ppm | 20 ppm | 40 ppm | 60 ppm | 80 ppm |
| PGC Concentration | 0 ppm | | 3.14 | >4.44 | >4.44 | >4.44 | >4.44 |
| | 10 ppm | 0.21 | >4.44 | >4.44 | >4.44 | >4.44 | >4.44 |
| | 25 ppm | 0.06 | >4.44 | >4.44 | >4.44 | >4.44 | >4.44 |
| | 50 ppm | 0.07 | >4.44 | >4.44 | >4.44 | >4.44 | >4.44 |
| | 100 ppm | 0.04 | >4.44 | >4.44 | >4.44 | >4.44 | >4.44 |
| | 200 ppm | 0.08 | >4.44 | >4.44 | >4.44 | >4.44 | >4.44 |

Concentrations of Didecyl dimethyl ammonium chloride and PGC were tested against *C. albicans* and *A. brasiliensis*. In the following, the log reductions against each microorganism is provided.

*C. albicans*—

| | | Didecyl dimethyl ammonium chloride Concentration | | | | | |
|---|---|---|---|---|---|---|---|
| | | 0 ppm | 10 ppm | 20 ppm | 30 ppm | 40 ppm | 50 ppm |
| PGC Concentration | 0 ppm | | 1.07 | 1.01 | 1.33 | 2.43 | >4.52 |
| | 10 ppm | 0.00 | 1.26 | 1.14 | 1.69 | 2.56 | >4.52 |
| | 25 ppm | 0.00 | 1.55 | 2.29 | 2.38 | 3.02 | >4.52 |
| | 50 ppm | 0.00 | 1.35 | 2.55 | 2.58 | 3.44 | >4.52 |
| | 100 ppm | 0.00 | 2.17 | 3.35 | 3.44 | >4.52 | >4.52 |
| | 200 ppm | 0.00 | 2.49 | 4.52 | 3.49 | >4.52 | >4.52 |

*A. brasiliensis*—

| | | Didecyl dimethyl ammonium chloride Concentration | | | | | |
|---|---|---|---|---|---|---|---|
| | | 0 ppm | 10 ppm | 20 ppm | 30 ppm | 40 ppm | 50 ppm |
| PGC Concentration | 0 ppm | | 1.01 | 2.44 | >4.05 | >4.05 | >4.05 |
| | 10 ppm | 0.01 | 1.10 | 2.69 | >4.05 | >4.05 | >4.05 |
| | 25 ppm | −0.01 | 2.19 | 3.32 | >4.05 | >4.05 | >4.05 |
| | 50 ppm | 0.03 | 2.24 | >4.05 | >4.05 | >4.05 | >4.05 |
| | 100 ppm | 0.05 | 3.75 | >4.05 | >4.05 | >4.05 | >4.05 |
| | 200 ppm | 0.02 | 3.92 | >4.05 | >4.05 | >4.05 | >4.05 |

Concentrations of Sodium Benzoate and PGC were tested against *P. gergoviae, C. albicans*, and *A. brasiliensis*. In the following, the log reductions against each microorganism is provided.

*P. gergoviae*—

| | | Sodium Benzoate Concentration | | | | | |
|---|---|---|---|---|---|---|---|
| | | 0 ppm | 2000 ppm | 5000 ppm | 10000 ppm | 20000 ppm | 30000 ppm |
| PGC Concentration | 0 ppm | | 0.00 | 0.00 | 0.00 | 0.46 | 1.40 |
| | 5 ppm | 0.00 | 0.00 | 0.00 | 0.00 | 0.62 | 1.43 |
| | 12.5 ppm | 0.00 | 0.00 | 0.00 | 0.00 | 0.58 | 1.51 |
| | 25 ppm | 0.00 | 0.00 | 0.00 | 0.07 | 1.29 | 1.50 |
| | 50 ppm | 0.00 | 0.00 | 0.00 | 0.04 | 1.31 | 1.67 |
| | 100 ppm | 0.00 | 0.00 | 0.00 | 0.23 | 1.34 | 2.16 |

*C. albicans*—

| | | Sodium Benzoate Concentration | | | | | |
|---|---|---|---|---|---|---|---|
| | | 0 ppm | 10000 ppm | 20000 ppm | 30000 ppm | 40000 ppm | 50000 ppm |
| PGC Concentration | 0 ppm | | 0.00 | 0.00 | 0.00 | 0.00 | 2.06 |
| | 10 ppm | 0.00 | 0.00 | 0.00 | 0.00 | 0.00 | 2.11 |
| | 25 ppm | 0.00 | 0.00 | 0.00 | 0.00 | 0.00 | 2.16 |
| | 50 ppm | 0.00 | 0.00 | 0.00 | 0.00 | 0.00 | 2.44 |
| | 100 ppm | 0.00 | 0.00 | 0.00 | 0.00 | 0.00 | 2.62 |
| | 200 ppm | 0.00 | 0.00 | 0.00 | 0.00 | 0.00 | 3.85 |

*A. brasiliensis*—

| | | Sodium Benzoate Concentration | | | | | |
|---|---|---|---|---|---|---|---|
| | | 0 ppm | 10000 ppm | 20000 ppm | 30000 ppm | 40000 ppm | 50000 ppm |
| PGC Concentration | 0 ppm | | 0.17 | 0.50 | 0.70 | 1.32 | 1.34 |
| | 10 ppm | 0.00 | 0.22 | 0.46 | 0.97 | 1.32 | 1.50 |
| | 25 ppm | 0.00 | 0.25 | 0.58 | 0.73 | 1.40 | 1.43 |
| | 50 ppm | −0.02 | 0.27 | 0.53 | 1.17 | 1.32 | 1.58 |
| | 100 ppm | 0.01 | 0.33 | 0.80 | 1.23 | 1.38 | 1.62 |
| | 200 ppm | −0.01 | 0.44 | 1.23 | 1.53 | 1.38 | 1.53 |

Concentrations of Lactic Acid and PGC were tested against *P. gergoviae*, and *A. brasiliensis*. In the following, the log reductions against each microorganism is provided.

*P. gergoviae*—

| | | Lactic Acid Concentration | | | | | |
|---|---|---|---|---|---|---|---|
| | | 0 ppm | 200 ppm | 500 ppm | 1000 ppm | 1500 ppm | 2000 ppm |
| PGC Concentration | 0 ppm | | 0.00 | 0.00 | 2.08 | 3.67 | 4.49 |
| | 10 ppm | 0.00 | 0.00 | 0.00 | 2.16 | 3.84 | 4.55 |
| | 25 ppm | 0.00 | 0.00 | 0.00 | 2.85 | 3.94 | 4.58 |
| | 50 ppm | 0.00 | 0.00 | 0.00 | 3.47 | 4.33 | 5.09 |
| | 100 ppm | 0.00 | 0.00 | 2.00 | 3.59 | 4.65 | >5.52 |
| | 200 ppm | 0.00 | 0.00 | 2.31 | 4.33 | >5.52 | >5.52 |

*A. brasiliensis*—

| | | Lactic Acid Concentration | | | | | |
|---|---|---|---|---|---|---|---|
| | | 0 ppm | 100 ppm | 250 ppm | 500 ppm | 1000 ppm | 2500 ppm |
| PGC Concentration | 0 ppm | | 0.06 | 0.12 | 0.05 | 0.08 | 0.15 |
| | 10 ppm | −0.01 | 0.00 | −0.02 | 0.01 | 0.09 | 0.39 |
| | 25 ppm | −0.03 | 0.03 | 0.02 | 0.09 | 0.41 | 0.59 |
| | 50 ppm | −0.01 | 0.02 | 0.18 | 0.36 | 1.16 | 1.08 |
| | 100 ppm | −0.03 | 0.00 | 0.54 | 0.91 | 1.22 | 1.01 |
| | 200 ppm | 0.09 | 0.19 | 0.85 | 0.85 | 1.08 | 1.14 |

Concentrations of Benzyl Alcohol and PGC were tested against *P. gergoviae*. In the following, the log reductions against *P. gergoviae* is provided.

*P. gergoviae*—

| | | Benzyl Alcohol Concentration | | | | | |
|---|---|---|---|---|---|---|---|
| | | 0 ppm | 500 ppm | 1000 ppm | 2000 ppm | 3000 ppm | 4000 ppm |
| PGC Concentration | 0 ppm | | 0.00 | 1.24 | 1.57 | 2.04 | 4.04 |
| | 10 ppm | 0.00 | 0.00 | 1.24 | 1.58 | 1.88 | 3.92 |
| | 25 ppm | 0.00 | 0.00 | 1.23 | 1.54 | 1.96 | 3.68 |
| | 50 ppm | 0.00 | 0.00 | 1.30 | 1.48 | 1.97 | 3.66 |
| | 100 ppm | 0.00 | 1.39 | 1.38 | 1.61 | 2.03 | 3.65 |
| | 200 ppm | 0.00 | 1.58 | 1.45 | 1.50 | 1.88 | 3.63 |

Concentrations of Phenoxyethanol and PGC were tested against *P. gergoviae, C. albicans*, and *A. brasiliensis*. In the following, the log reductions against each microorganism is provided.

*P. gergoviae*—

| | | Phenoxyethanol Concentration | | | | | |
|---|---|---|---|---|---|---|---|
| | | 0 ppm | 1000 ppm | 2500 ppm | 5000 ppm | 7500 ppm | 10000 ppm |
| PGC Concentration | 0 ppm | | 0.00 | 0.00 | 0.00 | 0.00 | 0.52 |
| | 10 ppm | 0.00 | 0.00 | 0.00 | 0.00 | 0.00 | 1.66 |
| | 25 ppm | 0.00 | 0.00 | 0.00 | 0.00 | 0.00 | 1.78 |
| | 50 ppm | 0.00 | 0.00 | 0.00 | 0.00 | 0.08 | 2.58 |
| | 100 ppm | 0.00 | 0.00 | 0.00 | 0.00 | 0.85 | 3.89 |
| | 200 ppm | 0.00 | 0.00 | 0.00 | 0.06 | 2.49 | >5.52 |

*C. albicans*—

| | | Phenoxyethanol Concentration | | | | | |
|---|---|---|---|---|---|---|---|
| | | 0 ppm | 1000 ppm | 2500 ppm | 5000 ppm | 7500 ppm | 10000 ppm |
| PGC Concentration | 0 ppm | | 0.00 | 0.00 | 0.00 | 0.00 | 0.00 |
| | 10 ppm | 0.00 | 0.00 | 0.00 | 0.00 | 0.00 | 0.00 |
| | 25 ppm | 0.00 | 0.00 | 0.00 | 0.00 | 0.00 | 0.00 |
| | 50 ppm | 0.00 | 0.00 | 0.00 | 0.00 | 0.00 | 0.00 |
| | 100 ppm | 0.00 | 0.00 | 0.00 | 0.00 | 0.00 | 0.46 |
| | 200 ppm | 0.00 | 0.00 | 0.00 | 0.00 | 0.00 | 1.73 |

*A. brasiliensis*—

| | | Phenoxyethanol Concentration | | | | | |
|---|---|---|---|---|---|---|---|
| | | 0 ppm | 1000 ppm | 2500 ppm | 5000 ppm | 7500 ppm | 10000 ppm |
| PGC Concentration | 0 ppm | | 0.01 | −0.07 | 0.03 | 0.08 | 0.50 |
| | 10 ppm | 0.00 | −0.02 | −0.02 | 0.04 | 0.11 | 0.20 |
| | 25 ppm | 0.00 | 0.01 | −0.01 | 0.06 | 0.09 | 0.42 |
| | 50 ppm | −0.02 | 0.02 | −0.04 | 0.04 | 0.19 | 0.38 |
| | 100 ppm | 0.01 | 0.06 | −0.03 | 0.10 | 0.31 | 1.00 |
| | 200 ppm | −0.01 | 0.03 | 0.07 | 0.27 | 0.51 | 1.02 |

Concentrations of Benzisothiazolinone and PGC were tested against *P. gergoviae, C. albicans*, and *A. brasiliensis*. In the following, the log reductions against each microorganism is provided.

*P. gergoviae*—

| | | Benzisothiazolinone Concentration | | | | | |
|---|---|---|---|---|---|---|---|
| | | 0 ppm | 12.5 ppm | 25 ppm | 50 ppm | 100 ppm | 200 ppm |
| PGC Concentration | 0 ppm | | 0.00 | 0.00 | 0.00 | 0.03 | 1.21 |
| | 10 ppm | 0.00 | 0.00 | 0.00 | 0.00 | 0.55 | 1.43 |
| | 25 ppm | 0.00 | 0.00 | 0.00 | 0.00 | 0.55 | 1.61 |
| | 50 ppm | 0.00 | 0.00 | 0.00 | 0.00 | 1.26 | 2.03 |
| | 100 ppm | 0.00 | 0.00 | 0.00 | 0.00 | 1.43 | 2.35 |
| | 200 ppm | 0.00 | 0.00 | 0.00 | 0.06 | 1.52 | 3.22 |

*C. albicans*—

| | | Benzisothiazolinone Concentration | | | | | |
|---|---|---|---|---|---|---|---|
| | | 0 ppm | 50 ppm | 100 ppm | 250 ppm | 500 ppm | 1000 ppm |
| PGC Concentration | 0 ppm | | 0.00 | 0.00 | 0.00 | 0.00 | 0.00 |
| | 10 ppm | 0.00 | 0.00 | 0.00 | 0.00 | 0.00 | 0.00 |
| | 25 ppm | 0.00 | 0.00 | 0.00 | 0.00 | 0.00 | 0.00 |
| | 50 ppm | 0.00 | 0.00 | 0.00 | 0.00 | 0.00 | 0.13 |
| | 100 ppm | 0.00 | 0.00 | 0.00 | 0.00 | 0.03 | 0.35 |
| | 200 ppm | 0.00 | 0.00 | 0.00 | 0.00 | 0.60 | 0.58 |

*A. brasiliensis*—

| | | Benzisothiazolinone Concentration | | | | | |
|---|---|---|---|---|---|---|---|
| | | 0 ppm | 50 ppm | 100 ppm | 250 ppm | 500 ppm | 1000 ppm |
| PGC Concentration | 0 ppm | | −0.03 | 0.17 | 0.14 | 0.24 | 0.28 |
| | 10 ppm | 0.00 | 0.04 | 0.18 | 0.27 | 0.39 | 0.38 |
| | 25 ppm | 0.00 | 0.08 | 0.39 | 0.37 | 0.30 | 0.50 |

-continued

| | Benzisothiazolinone Concentration | | | | | |
|---|---|---|---|---|---|---|
| | 0 ppm | 50 ppm | 100 ppm | 250 ppm | 500 ppm | 1000 ppm |
| 50 ppm | −0.02 | 0.12 | 0.53 | 0.56 | 0.77 | 0.36 |
| 100 ppm | 0.01 | 0.04 | 0.53 | 0.64 | 0.80 | 0.71 |
| 200 ppm | −0.01 | 0.27 | 0.69 | 1.02 | 1.00 | 1.04 |

Concentrations of Sorbic acid and PGC were tested against *P. gergoviae*. In the following, the log reductions against each microorganism is provided.

*P. gergoviae*—

| | | Sorbic acid Concentration | | | | | |
|---|---|---|---|---|---|---|---|
| | | 0 ppm | 100 ppm | 200 ppm | 300 ppm | 400 ppm | 500 ppm |
| PGC Concen-tration | 0 ppm | | 0.00 | 0.00 | 0.00 | 0.58 | 1.38 |
| | 10 ppm | 0.00 | 0.00 | 0.00 | 0.55 | 1.43 | 2.35 |
| | 25 ppm | 0.00 | 0.03 | 0.46 | 3.00 | 3.22 | 5.22 |
| | 50 ppm | 0.00 | 1.28 | 2.62 | >5.52 | >5.52 | >5.52 |
| | 100 ppm | 0.00 | 5.22 | >5.52 | >5.52 | >5.52 | >5.52 |
| | 200 ppm | 0.00 | >5.52 | >5.52 | >5.52 | >5.52 | >5.52 |

Concentrations of Dehydroacetic acid and PGC were tested against *C. albicans*. In the following, the log reductions against each microorganism is provided.

*C. albicans*—

| | | Dehydroacetic acid concentration | | | | | |
|---|---|---|---|---|---|---|---|
| | | 0 ppm | 1000 ppm | 2000 ppm | 3000 ppm | 4000 ppm | 5000 ppm |
| PGC Concen-tration | 0 ppm | | 0.00 | 0.00 | 0.00 | 0.23 | 0.52 |
| | 10 ppm | 0.00 | 0.00 | 0.00 | 0.00 | 0.30 | 0.81 |
| | 25 ppm | 0.00 | 0.00 | 0.00 | 0.33 | 0.62 | 1.35 |
| | 50 ppm | 0.00 | 0.00 | 0.18 | 0.46 | 1.20 | 1.62 |
| | 100 ppm | 0.00 | 0.00 | 0.15 | 0.62 | 1.19 | 1.42 |
| | 200 ppm | N/A | 0.00 | 0.06 | 0.33 | 1.35 | 1.39 |

Example 4

The following tests were completed in order to demonstrate the effectiveness of various alkylene glycol esters when combined with phenoxyethanol (PHE).

In this example, various different alkylene glycol esters were combined with phenoxyethanol and tested against *Pluralibacter gergoviae* ATCC 33028/DSM 9245.

Method

Test Organism Preparation

*Pluralibacter gergoviae* was kept cryofrozen at −80° C.; before use, they were sub-cultured onto tryptone soya agar, and incubated at the appropriate temperature and time.

The incubation conditions used for microorganism growth are summarized in Table 8.

TABLE 8

| Micro-organisms | Agar | Temp (° C.) | Time |
|---|---|---|---|
| *Pluralibacter gergoviae* ATCC 33028 | TSA | 30 ± 2 | 24 ± 2 hours |

A test suspension was then created by adding loopfuls of organism to sterile distilled water and adjusting the cell concentration to between $1\times10^9$ and $5\times10^9$ CFU/ml.

To establish the precise CFU/ml of the inoculum culture a 1 ml aliquot was then taken from the inoculum suspension and serially diluted down to $10^{-8}$, 1 ml of each dilution was then plated in duplicate using the pour plate method and incubated at the appropriate temperature and time.

Test Sample Preparation

For each organism tested, 1 g of each PHE (phenoxyethanol) and AGE (alkylene glycol caprylate) composition sample was prepared in sterile distilled water. The samples used in this study are summarized in Table 9.

TABLE 9

| Sample | AGE | AGE concen-tration (ppm) | PHE concen-tration (ppm) |
|---|---|---|---|
| PHE Control | N/A | N/A | 6000 |
| Propyleneglycol caprylate test | Propyleneglycol caprylate | 1000 | 6000 |
| Ethyleneglycol caprylate test | Ethyleneglycol caprylate | 1000 | 6000 |
| Butyleneglycol caprylate test | Butyleneglycol caprylate | 1000 | 6000 |
| Dipropyleneglycol caprylate test | Dipropyleneglycol caprylate | 1000 | 6000 |
| Propyleneglycol Dodecanoate test | Propyleneglycol Dodecanoate | 1000 | 6000 |
| Propyleneglycol Caprate test | Propyleneglycol Caprate | 1000 | 6000 |
| Propyleneglycol Caproate test | Propyleneglycol Caproate | 1000 | 6000 |

Test Procedure

Each test sample was prepared by inoculating 1 ml aliquot of the test organism suspension into 1 ml of test sample.

The combination was then mixed. Each test mixture was sampled and tested at a defined time point after inoculation.

Upon reaching the specified contact time the test mixture was deactivated by adding a 100 µl of test mixture into 900 µl of neutralizing broth and the whole solution was mixed. The solution was left for 5 minutes to ensure the action of the preservative agent was effectively neutralized. Subsequent dilutions were prepared by adding 100 µl into 900 µl of neutralizing broth.

For each dilution prepare drop plates using appropriate agar and incubate at the appropriate temperature and time as in Table 8.

Plating

Used the drop plate technique.

Prepare agar plates by drying for 45 min-1 hour in a laminar flow at 20-25° C. Aliquot 0.025 ml drops onto the agar surface for each sample dilution. Allow drops to dry and incubate appropriately.

Plates were plates were prepared in sextuplicate for each for each sample dilution.

Limits of Detection

Depending on the dilution parameters of a method and the techniques used to enumerate cells, specific limits of detection must be set to ensure reliable enumeration.

For counting of drop plates, colonies from the incubated plates were enumerated using the lower count limit of <0.25 CFU/0.025 ml and the upper count limit of >8.25 CFU/0.025 ml across all 6 drops. When dilution factors are taken into account this results in a lower limit of <10 CFU/ml and an upper limit of >330 CFU/ml.

The upper and lower limits for drop plating were only employed on the highest and lowest dilution factor plates.

For example if the lowest dilution plate e.g. 10–1 had a mean of 0 visible colonies, <0.25 would be recorded and 0.25 would be used for the calculation.

Similarly for the upper limit on the highest dilution plate e.g. 10–4, had a mean of 31 colonies counted and >8.25 would be recorded and 8.25 would be used for the calculation.

The lowest dilution factor plate used was $10^1$. The highest dilution factor plate used was $10^{-7}$.

When reporting the final log reduction value, if a lower limit of detection has been used to make the calculation a ">" value will be reported for example ">5.02 log reduction", while if upper limit of detection has been used to make the calculation a "<" value will be reported for example "<2.92 log reduction".

Calculation of Recovery:

The recovery count per ml of sample is calculated as follows:

Enumeration and Calculation of N (Inoculum Culture)

Because there is a 1 in 2 dilution of the inoculum culture when added to the product during the test, the count per ml of sample is calculated as follows:

Organisms per ml inoculum culture/2=organisms CFU per ml sample.

Enumeration and Calculation of T (Test Sample)

First, the mean average of cfu per 0.025 ml spots was established using the below calculation;

$$T = \left(\frac{d_1}{6}\right)$$

Where $d_1$ is sum of viable count values from 6 drops

This was then multiplied by 40 to establish cfu/ml;

Both N (inoculum culture) and T (Test sample) underwent a number of dilutions. To account for this a final multiplication of the dilution factor is applied to both.

Log Reduction Calculations (N_T)

Before calculating the log reduction both N and T were converted into a logarithm base 10 value.

To calculate the final log reduction the following calculation was used:

$$\text{Log } 10N - \log 10T = \log \text{ reduction}$$

Results

The following table illustrates the Log reduction of the different combinations compared to the PHE control, tested after 15 minutes, 30 minute, 1 hour and 2 hours.

| Sample | 15 min | 30 min | 1 hour | 2 hour |
|---|---|---|---|---|
| PHE Control | −0.05 | −0.15 | −0.19 | 0.00 |
| Propyleneglycol caprylate test | 0.00 | 0.27 | 3.55 | >7.30 |
| Ethyleneglycol caprylate test | 2.70 | >7.30 | >7.30 | >7.30 |
| Butyleneglycol caprylate test | 0.55 | 0.84 | 5.00 | >7.30 |
| Dipropyleneglycol caprylate test | 0.55 | 1.36 | 4.33 | 5.30 |
| Propyleneglycol Dodecanoate test | 0.32 | 0.53 | 0.81 | 1.18 |
| Propyleneglycol Caprate test | 1.06 | 2.42 | 3.78 | 6.06 |
| Propyleneglycol Caproate test | 0.32 | 0.48 | 1.26 | 3.25 |

As shown above, all of the tested alkylene glycol esters demonstrated effectiveness.

What is claimed:

1. A preservative composition comprising (i) a preservative agent selected from the group consisting of phenoxyethanol, bis (3-aminopropyl) dodecylamine, didecyl dimethyl ammonium chloride, sodium benzoate, lactic acid, benzyl alcohol, benzisothiazaolinone, sorbic acid, and dehydroacetic acid, or a salt thereof; and (ii) a mixture of at least one propylene glycol monocaprylate and propylene glycol dicaprylate;

wherein the mixture of at least one propylene glycol monocaprylate and propylene glycol dicaprylate is present in an amount to sufficiently increase the efficacy of the preservative agent as compared to the preservative agent alone.

2. The preservative composition according to claim 1, wherein the preservative agent is phenoxyethanol and wherein the phenoxyethanol and the mixture of at least one propylene glycol monocaprylate and propylene glycol dicaprylate are comprised in the preservative composition at a weight ratio of from 6:1 to 1:1.

3. The preservative composition according to claim 1, wherein the preservative agent is bis(3-aminopropyl) dodecylamine and wherein the bis(3-aminopropyl) dodecylamine and the mixture of at least one propylene glycol monocaprylate and propylene glycol dicaprylate are comprised in the preservative composition at a weight ratio of from 25:1 to 1:25.

4. The preservative composition according to claim 1, wherein the preservative agent is didecyl dimethyl ammonium chloride and wherein the didecyl dimethyl ammonium chloride and the mixture of at least one propylene glycol monocaprylate and propylene glycol dicaprylate are comprised in the preservative composition at a weight ratio of from 25:1 to 1:25.

5. The preservative composition according to claim 1, wherein the preservative agent is sodium benzoate and wherein the sodium benzoate and the mixture of at least one propylene glycol monocaprylate and propylene glycol dicaprylate are comprised in the preservative composition at a weight ratio of from 50,000:1 to 50:1.

6. The preservative composition according to claim 1, wherein the preservative agent is lactic acid and wherein the lactic acid and the mixture of at least one propylene glycol monocaprylate and propylene glycol dicaprylate are comprised in the preservative composition at a weight ratio of from 250:1 to 1:1.

7. The preservative composition according to claim 1, wherein the preservative agent is benzyl alcohol and wherein the benzyl alcohol and the mixture of at least one propylene glycol monocaprylate and propylene glycol dicaprylate are comprised in the preservative composition at a weight ratio of from 800:1 to 1:1.

8. The preservative composition according to claim 1, wherein the preservative agent is benzisothiazolinone and wherein the benzisothiazolinone and the mixture of at least one propylene glycol monocaprylate and propylene glycol dicaprylate are comprised in the preservative composition at a weight ratio of from 100:1 to 1:4.

9. The preservative composition according to claim 1, wherein the preservative agent is sorbic acid and wherein the sorbic acid and the mixture of at least one propylene glycol monocaprylate and propylene glycol dicaprylate are comprised in the preservative composition at a weight ratio of from 100:1 to 1:4:4.

10. The preservative composition according to claim 1, wherein the preservative agent is dehydroacetic acid and wherein the dehydroacetic acid and the mixture of at least one propylene glycol monocaprylate and propylene glycol dicaprylate are comprised in the preservative composition at a weight ratio of from 1000:1 to 10:1.

11. The preservative composition according to claim 1, wherein the at least one propylene glycol monocaprylate and the propylene glycol dicaprylate are comprised in the mixture at a weight ratio of from 15:1 to 1:1.

12. The preservative composition according to claim 1, wherein the preservative agent is phenoxyethanol, wherein the phenoxyethanol and the mixture of at least one propylene glycol monocaprylate and propyleneglycol dicaprylate are comprised in the preservative composition at a weight ratio of from 1:1 to 2:1.

13. The preservative composition according to claim 1, wherein the mixture of at least one propylene glycol monocaprylate and propylene glycol dicaprylate comprises at least 50% by weight of at least one propylene glycol monocaprylate, based on the total weight of the mixture of at least one propylene glycol monocaprylate and propylene glycol dicaprylate.

14. The preservative composition according to claim 1, wherein the at least one propyleneglycol monocaprylate is selected from octanxic acid-2-hydroxy-1-methylethyl ester, 2-hydroxylpropyl caprylate, and a combination thereof; and/or the propylene glycol dicaprylate is 1,2-propylene glycol dicaprylate.

15. A personal care product or a home care formulation comprising the preservative composition according claim 1.

16. The personal care product or a home care formulation according to claim 15, wherein the mixture of at least one propylene glycol monocaprylate and propylene glycol dicaprylate comprised in the preservative composition is present in the personal care product in an amount of from 1 wt.-% or less, based on the weight of the personal care product or home care formulation.

17. An end-use formulation comprising the preservative composition according to claim 1.

18. A method for preventing a personal care product or a home care formulation from spoilage by microorganisms, the method comprising adding the preservative composition according to claim 1 to the personal care product or the home care formulation.

19. A method for increasing the efficacy of a preservative agent against microorganisms in an end-use formulation, said method comprising providing an end-use formulation and a preservative agent, adding an effective amount of a mixture of at least one propylene glycol monocaprylate and propylene glycol dicaprylate to the preservative agent and end use formulation to increase the efficacy of the preservative agent in the end-use formulation, as compared to an equal amount of preservative agent without the mixture of at least one propylene glycol monocaprylate and propylene glycol dicaprylate in the end-use formulation, wherein the preservative agent is selected from the group consisting of phenoxyethanol, bis(3-aminopropyl) dodecylamine, didecyl dimethyl ammonium chloride, sodium benzoate, lactic acid, benzyl alcohol, benzisothiazolinone, sorbic acid, and dehydroacetic acid, or a salt thereof.

20. The method of claim 19, wherein the mixture of at least one propylene glycol monocaprylate and propylene glycol dicaprylate comprises a mixture of octanoic acid-2-hydroxy-1-methylethyl ester, 2-hydroxylpropyl caprylate, and 1,2-propylene glycol dicaprylate.

21. The method of claim 19, wherein the preservative agent is phenoxyethanol.

22. The method of claim 19, wherein the efficacy is increased by at least 0.5 log reduction.

23. A preservative composition comprising (i) phenoxyethanol; and (ii) a mixture of at least one propylene glycol monocaprylate and propyleneglycol dicaprylate;

wherein phenoxyethanol and the mixture of at least one propylene glycol monocaprylate and propylene glycol dicaprylate are comprised in the preservative composition at a weight ratio of from 1:1 to 6:1.

24. The preservative composition according to claim 23, wherein phenoxyethanol and the mixture of at least one propylene glycol monocaprylate and propylene glycol dicaprylate are comprised in the preservative composition at a weight ratio of from 1:1 to 2:1.

25. The preservative composition according to claim 23, wherein the at least one propylene glycol monocaprylate and the propylene glycol dicaprylate are comprised in the mixture at a weight ratio of from 15:1 to 1:1.

26. The preservative composition according to claim 23, wherein the at least one propylene glycol monocaprylate is selected from octanxic acid-2-hydroxy-1-methylethyl ester, 2-hydroxylpropyl caprylate, and a combination thereof; and/or the propylene glycol dicaprylate is 1,2-propyleneglycol dicaprylate.

27. A personal care product or a home care formulation comprising the preservative composition according to claim 23.

28. The personal care product or home care formulation according to claim 27, wherein the mixture of at least one propylene glycol monocaprylate and propylene glycol dicaprylate comprised in the preservative composition is present in the personal care product in an amount of from 1 wt.-% or less, based on the weight of the personal care product or home care formulation.

29. An end-use formulation comprising the preservative composition according to claim 23.

30. A method for preventing a personal care product or a home care formulation from spoilage by microorganisms, the method comprising adding the preservative composition according to claim 23 to the personal care product or home care formulation.

31. A method for increasing the efficacy of a preservative agent against microorganisms in an end-use formulation, the method comprising providing an end-use formulation and a preservative agent, adding an effective amount of a mixture of at least one propylene glycol monocaprylate and propylene glycol dicaprylate to the preservative agent and end use formulation to increase the efficacy of the preservative agent in the end-use formulation, as compared to an equal amount of preservative agent without the mixture of at least one propylene glycol monocaprylate and propylene glycol dicaprylate in the end-use formulation, wherein the preservative agent is phenoxyethanol, and wherein the weight ratio of phenoxyethanol and the mixture of at least one propylene glycol monocaprylate and propylene glycol dicaprylate is from 1:1 to 6:1.

32. The method according to claim 31, wherein the efficacy is increased by at least 0.5 log reduction.

* * * * *